US010801024B2

(12) United States Patent
Ozes et al.

(10) Patent No.: US 10,801,024 B2
(45) Date of Patent: Oct. 13, 2020

(54) INHIBITION OF LNCRNA HOTAIR AND RELATED MATERIALS AND METHODS

(71) Applicant: Indiana University Research and Technology Corporation, Indianapolis, IN (US)

(72) Inventors: Ali Rayet Ozes, San Bruno, CA (US); Kenneth P. Nephew, Bloomington, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 117 days.

(21) Appl. No.: 15/575,321

(22) PCT Filed: May 20, 2016

(86) PCT No.: PCT/US2016/033611
§ 371 (c)(1),
(2) Date: Nov. 17, 2017

(87) PCT Pub. No.: WO2016/187578
PCT Pub. Date: Nov. 24, 2016

(65) Prior Publication Data
US 2018/0148720 A1 May 31, 2018

Related U.S. Application Data

(60) Provisional application No. 62/164,296, filed on May 20, 2015, provisional application No. 62/298,902, filed on Feb. 23, 2016.

(51) Int. Cl.

| | |
|---|---|
| ***C12N 15/11*** | (2006.01) |
| ***C12N 15/113*** | (2010.01) |
| ***A61K 31/7115*** | (2006.01) |
| ***A61K 45/06*** | (2006.01) |
| ***A61P 35/00*** | (2006.01) |
| ***C12Q 1/6883*** | (2018.01) |
| ***A61P 19/02*** | (2006.01) |
| ***C12Q 1/6886*** | (2018.01) |
| ***A61K 31/7125*** | (2006.01) |

(52) U.S. Cl.
CPC ........ *C12N 15/113* (2013.01); *A61K 31/7115* (2013.01); *A61K 31/7125* (2013.01); *A61K 45/06* (2013.01); *A61P 19/02* (2018.01); *A61P 35/00* (2018.01); *C12Q 1/6883* (2013.01); *C12Q 1/6886* (2013.01); *C12N 2310/113* (2013.01); *C12N 2310/14* (2013.01); *C12N 2310/20* (2017.05); *C12N 2310/3181* (2013.01); *C12N 2310/3513* (2013.01); *C12Q 2600/118* (2013.01)

(58) Field of Classification Search
None
See application file for complete search history.

(56) References Cited

U.S. PATENT DOCUMENTS

| | | | | |
|---|---|---|---|---|
| 2010/0279302 | A1 | 11/2010 | Segal et al. | |
| 2012/0039990 | A1 | 2/2012 | Reshetnyak et al. | |
| 2013/0108686 | A1 | 5/2013 | Eritja Casadella et al. | |
| 2015/0141320 | A1* | 5/2015 | Krieg ................. | A61K 31/7088 514/1.1 |

FOREIGN PATENT DOCUMENTS

| | | | | |
|---|---|---|---|---|
| WO | WO-0220716 A2 * | 3/2002 | ......... | C12N 15/1137 |

OTHER PUBLICATIONS

International Preliminary Report on Patentability issued by The International Bureau of WIPO, dated Nov. 21, 2017, for International Application No. PCT/US2016/033611; 11 pages.
International Search Report and Written Opinion issued by the ISA/US, Commissioner for Patents, dated Oct. 14, 2016, for International Application No. PCT/US2016/033611; 14 pages.
Bhan, Arunoday, et al., "Antisense-transcript long noncoding RNA (lncRNA) HOTAIR is transcriptionally induced by estradiol," J Mol Biol., Oct. 9, 2013, vol. 425, No. 19; pp. 3707-3722.
Ferenc, G., et al., "A Convenient Method for the Synthesis of Oligonucleotide-Cationic Peptide Conjugates," Nucleosides, Nucleotides, and Nucleic Acids, (2005), vol. 24, No. 5-7; pp. 1059-1061.

* cited by examiner

*Primary Examiner* — Ekaterina Poliakova-Georgantas
(74) *Attorney, Agent, or Firm* — Faegre Drinker Biddle & Reath LLP

(57) ABSTRACT

Embodiments disclosed herein concern compositions and methods for treating a condition characterized by overexpression of long non-coding RNA HOTAIR. In certain embodiments, synthetic polynucleotide analogs capable of hybridizing with a target sequence domain of HOTAIR are provided. The synthetic polynucleotide analogs can be formulated into a pharmaceutical composition for treating a subject having or at risk of having a condition characterized by HOTAIR overexpression. In certain embodiments, the pharmaceutical composition can resensitize a subject to a chemotherapeutic agent. Other embodiments concern uses for HOTAIR-targeting synthetic polynucleotide analogs, including methods for determining HOTAIR expression in a sample.

17 Claims, 23 Drawing Sheets

Specification includes a Sequence Listing.

89 mer minimum region of HOTAIR
Wu et al. Biochemistry 2014.

5'GGAACGGAUUUAGAAGCCUGCAGUAGGGGAGUGGGGAGUGGAGAGAGGGAGCCCAGAG
UUACAGACGGCGGCGAGAGGAAGGAGGGGCG-3'

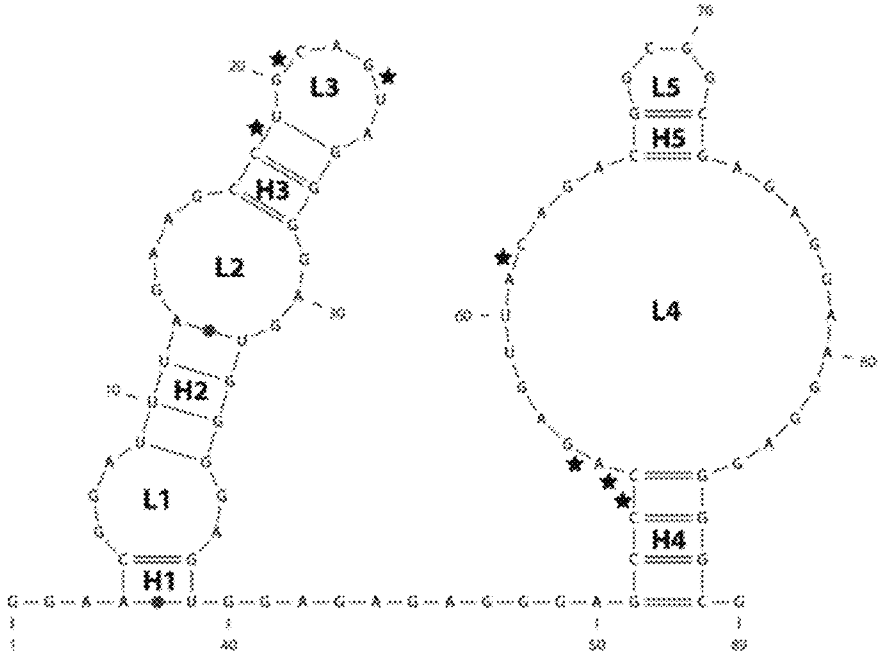

Star regions are shown Ezh2-Eed binding sites.

Red: Ezh2 and Eed binding regions
Green: Possible quadraplex-like structured region.

| | ACTUAL SEQUENCE |
|---|---|
| PNA target 1: | 5'-GCCUGCAGUA-3' |
| PNA target 2: | 5'-CCCAGAGUUAC-3' |
| PNA target 3: | 5'-GAGUUACAGA-3' |
| PNA target 4: | 5'-GCAGUAGGGGAG-3' |
| PNA target 5: | 5'-GGAGAGAGGG-3' |

| RNA TO DNA | | REVERSE COMPLEMENT (Actual PNA sequence) |
|---|---|---|
| GCCTGCAGTA | RC→ | 5'- TACTGCAGGC -3' |
| CCCAGAGTTAC | RC→ | 5'- GTAACTCTGGG -3' |
| GAGTTACAGA | RC→ | 5'- TCTGTAACTC -3' |
| GCAGTAGGGGAG | RC→ | 5'- CTCCCCTACTGC -3' |
| GGAGAGAGGG | RC→ | 5'- CCCTCTCTCC -3' |

FIG. 1

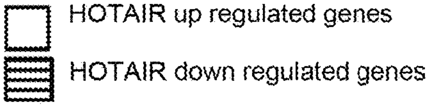
A2780_CR5
(Ovarian)
FIG. 4F
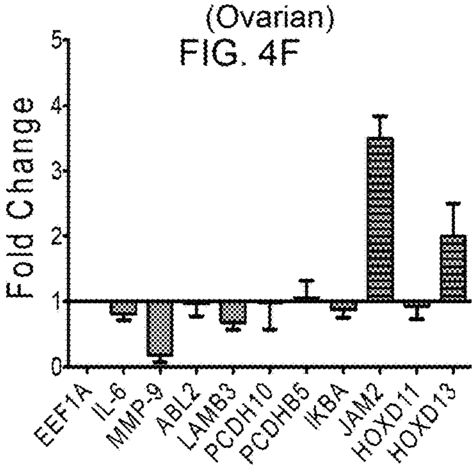
FIG. 5F
SKBR-3
(Breast)
FIG. 4G
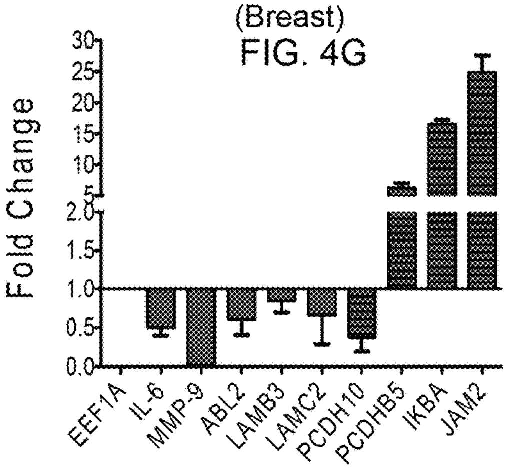
FIG. 5G Control PNA
PNA3

SEQUENCE LISTING

<160> NUMBER OF SEQ ID NOS: 55

<210> SEQ ID NO 1
<211> LENGTH: 89
<212> TYPE: RNA
<213> ORGANISM: Homo sapiens

<400> SEQUENCE: 1
ggaacggauu uagaagccug caguagggga guggggagug gagagaggga gcccagaguu 60
acagacggcg gcgagaggaa ggaggggcg 89

<210> SEQ ID NO 2
<211> LENGTH: 10
<212> TYPE: RNA
<213> ORGANISM: Homo sapiens

<400> SEQUENCE: 2
gccugcagua 10

<210> SEQ ID NO 3
<211> LENGTH: 11
<212> TYPE: RNA
<213> ORGANISM: Homo sapiens

<400> SEQUENCE: 3
cccagaguua c 11

<210> SEQ ID NO 4
<211> LENGTH: 10
<212> TYPE: RNA
<213> ORGANISM: Homo sapiens

<400> SEQUENCE: 4
gaguuacaga 10

<210> SEQ ID NO 5
<211> LENGTH: 12
<212> TYPE: RNA
<213> ORGANISM: Homo sapiens

<400> SEQUENCE: 5
gcaguagggg ag 12

<210> SEQ ID NO 6
<211> LENGTH: 10
<212> TYPE: RNA
<213> ORGANISM: Homo sapiens

<400> SEQUENCE: 6
ggagagaggg 10

<210> SEQ ID NO 7
<211> LENGTH: 10
<212> TYPE: DNA
<213> ORGANISM: Artificial sequence
<220> FEATURE:
<223> OTHER INFORMATION: Target domain 1 RNA (SEQ ID NO: 2) to DNA

<400> SEQUENCE: 7
gcctgcagta 10

<210> SEQ ID NO 8
<211> LENGTH: 11

-continued

```
<212> TYPE: DNA
<213> ORGANISM: Artificial sequence
<220> FEATURE:
<223> OTHER INFORMATION: Target domain 2 RNA (SEQ ID NO: 3) to DNA

<400> SEQUENCE: 8

cccagagtta c                                                            11


<210> SEQ ID NO 9
<211> LENGTH: 10
<212> TYPE: DNA
<213> ORGANISM: Artificial sequence
<220> FEATURE:
<223> OTHER INFORMATION: Target domain 3 RNA (SEQ ID NO: 4) to DNA

<400> SEQUENCE: 9

gagttacaga                                                              10


<210> SEQ ID NO 10
<211> LENGTH: 13
<212> TYPE: DNA
<213> ORGANISM: Artificial sequence
<220> FEATURE:
<223> OTHER INFORMATION: Target domain 4 RNA (SEQ ID NO: 5) to DNA

<400> SEQUENCE: 10

gcaggtaggg gag                                                          13


<210> SEQ ID NO 11
<211> LENGTH: 10
<212> TYPE: DNA
<213> ORGANISM: Artificial sequence
<220> FEATURE:
<223> OTHER INFORMATION: Target domain 5 RNA (SEQ ID NO: 6) to DNA

<400> SEQUENCE: 11

ggagagaggg                                                              10


<210> SEQ ID NO 12
<211> LENGTH: 10
<212> TYPE: DNA
<213> ORGANISM: Artificial sequence
<220> FEATURE:
<223> OTHER INFORMATION: Reverse complement of target domain 1 (SEQ ID
      NO: 3)

<400> SEQUENCE: 12

tactgcaggc                                                              10


<210> SEQ ID NO 13
<211> LENGTH: 11
<212> TYPE: DNA
<213> ORGANISM: Artificial sequence
<220> FEATURE:
<223> OTHER INFORMATION: Reverse complement of target domain 2 (SEQ ID
      NO: 3)

<400> SEQUENCE: 13

gtaactctgg g                                                            11


<210> SEQ ID NO 14
<211> LENGTH: 10
<212> TYPE: DNA
<213> ORGANISM: Artificial sequence
<220> FEATURE:
<223> OTHER INFORMATION: Reverse complement of target domain 3 (SEQ ID
      NO: 4)
```

<400> SEQUENCE: 14
tctgtaactc 10

<210> SEQ ID NO 15
<211> LENGTH: 12
<212> TYPE: DNA
<213> ORGANISM: Artificial sequence
<220> FEATURE:
<223> OTHER INFORMATION: Reverse complement of target domain 4 (SEQ ID NO: 5)

<400> SEQUENCE: 15
ctcccctact gc 12

<210> SEQ ID NO 16
<211> LENGTH: 10
<212> TYPE: DNA
<213> ORGANISM: Artificial sequence
<220> FEATURE:
<223> OTHER INFORMATION: Reverse complement of target domain 5 (SEQ ID NO: 6)

<400> SEQUENCE: 16
ccctctctcc 10

<210> SEQ ID NO 17
<211> LENGTH: 10
<212> TYPE: DNA
<213> ORGANISM: Artificial sequence
<220> FEATURE:
<223> OTHER INFORMATION: Artificial control sequence

<400> SEQUENCE: 17
ctcccttcaa 10

<210> SEQ ID NO 18
<211> LENGTH: 38
<212> TYPE: PRT
<213> ORGANISM: Artificial sequence
<220> FEATURE:
<223> OTHER INFORMATION: pH-sensitive tumor-targeting pH Low-Insertion Peptide (pHLIP)
<220> FEATURE:
<221> NAME/KEY: MISC_FEATURE
<222> LOCATION: (37)..(37)
<223> OTHER INFORMATION: Xaa is a cysteine group derivatized with 3-nitro-2-pyridinesulphenyl (NPys)

<400> SEQUENCE: 18

Ala Ala Glu Gln Asn Pro Ile Tyr Trp Ala Arg Tyr Ala Asp Trp Leu
1 5 10 15

Phe Thr Thr Pro Leu Leu Leu Leu Asp Leu Ala Leu Leu Val Asp Ala
20 25 30

Asp Glu Gly Thr Xaa Gly
35

<210> SEQ ID NO 19
<211> LENGTH: 9
<212> TYPE: PRT
<213> ORGANISM: Artificial sequence
<220> FEATURE:
<223> OTHER INFORMATION: Cell penetrating peptide

<400> SEQUENCE: 19

Arg Arg Arg Gln Arg Arg Lys Lys Arg

-continued 1               5

<210> SEQ ID NO 20
<211> LENGTH: 44
<212> TYPE: DNA
<213> ORGANISM: Artificial sequence
<220> FEATURE:
<223> OTHER INFORMATION: HOTAIR RNAi forward primer

<400> SEQUENCE: 20
gtggtttatc ttgcacccct cattctcaag ccccagccag ggaa 44

<210> SEQ ID NO 21
<211> LENGTH: 44
<212> TYPE: DNA
<213> ORGANISM: Artificial sequence
<220> FEATURE:
<223> OTHER INFORMATION: HOTAIR RNAi reverse primer

<400> SEQUENCE: 21
ttccctggct ggggcttgag aatgaggggt gcaagataaa ccac 44

<210> SEQ ID NO 22
<211> LENGTH: 27
<212> TYPE: RNA
<213> ORGANISM: Artificial sequence
<220> FEATURE:
<223> OTHER INFORMATION: Human HOTAIR dsiRNA - Sense strand

<400> SEQUENCE: 22
uucuaaaucc guuccauucc acugcga 27

<210> SEQ ID NO 23
<211> LENGTH: 25
<212> TYPE: RNA
<213> ORGANISM: Artificial sequence
<220> FEATURE:
<223> OTHER INFORMATION: Human HOTAIR dsiRNA - Antisense strand

<400> SEQUENCE: 23
gcaguggaau ggaacggauu uagaa 25

<210> SEQ ID NO 24
<211> LENGTH: 19
<212> TYPE: RNA
<213> ORGANISM: Artificial sequence
<220> FEATURE:
<223> OTHER INFORMATION: Negative control dsiRNA targeting GFP - Sense strand

<400> SEQUENCE: 24
cuacaacagc cacaacguc 19

<210> SEQ ID NO 25
<211> LENGTH: 19
<212> TYPE: RNA
<213> ORGANISM: Artificial sequence
<220> FEATURE:
<223> OTHER INFORMATION: Negative control dsiRNA targeting GFP - Antisense strand

<400> SEQUENCE: 25
gacguugugg cuguuguag 19

<210> SEQ ID NO 26
<211> LENGTH: 19

-continued

<212> TYPE: DNA
<213> ORGANISM: Artificial sequence
<220> FEATURE:
<223> OTHER INFORMATION: IL6R qPCR oligo - sense

<400> SEQUENCE: 26
tcactgggtg ctcaggaag 19

<210> SEQ ID NO 27
<211> LENGTH: 19
<212> TYPE: DNA
<213> ORGANISM: Artificial sequence
<220> FEATURE:
<223> OTHER INFORMATION: IL6R qPCR oligo - antisense

<400> SEQUENCE: 27
accagcaagt gcacagtcc 19

<210> SEQ ID NO 28
<211> LENGTH: 20
<212> TYPE: DNA
<213> ORGANISM: Artificial sequence
<220> FEATURE:
<223> OTHER INFORMATION: MMP9 qPCR oligo - sense

<400> SEQUENCE: 28
ttgacagcga caagaagtgg 20

<210> SEQ ID NO 29
<211> LENGTH: 20
<212> TYPE: DNA
<213> ORGANISM: Artificial sequence
<220> FEATURE:
<223> OTHER INFORMATION: MMP9 qPCR oligo - antisense

<400> SEQUENCE: 29
gccattcacg tcgtccttat 20

<210> SEQ ID NO 30
<211> LENGTH: 20
<212> TYPE: DNA
<213> ORGANISM: Artificial sequence
<220> FEATURE:
<223> OTHER INFORMATION: NFKBIA qPCR oligo - sense

<400> SEQUENCE: 30
gcaaaatcct gacctggtgt 20

<210> SEQ ID NO 31
<211> LENGTH: 20
<212> TYPE: DNA
<213> ORGANISM: Artificial sequence
<220> FEATURE:
<223> OTHER INFORMATION: NFKBA qPCR oligo - antisense

<400> SEQUENCE: 31
gctcgtcctc tgtgaactcc 20

<210> SEQ ID NO 32
<211> LENGTH: 20
<212> TYPE: DNA
<213> ORGANISM: Artificial sequence
<220> FEATURE:
<223> OTHER INFORMATION: IL6 qPCR oligo - sense

<400> SEQUENCE: 32 taccccagg agaagattcc 20

<210> SEQ ID NO 33
<211> LENGTH: 20
<212> TYPE: DNA
<213> ORGANISM: Artificial sequence
<220> FEATURE:
<223> OTHER INFORMATION: IL6 qPCR oligo - antisense

<400> SEQUENCE: 33
ttttctgcca gtgcctcttt 20

<210> SEQ ID NO 34
<211> LENGTH: 20
<212> TYPE: DNA
<213> ORGANISM: Artificial sequence
<220> FEATURE:
<223> OTHER INFORMATION: GAPDH qPCR oligo - sense

<400> SEQUENCE: 34
ccatcactgc cacccagaag 20

<210> SEQ ID NO 35
<211> LENGTH: 18
<212> TYPE: DNA
<213> ORGANISM: Artificial sequence
<220> FEATURE:
<223> OTHER INFORMATION: GAPDH qPCR oligo - antisense

<400> SEQUENCE: 35
ccttgcccac agccttgg 18

<210> SEQ ID NO 36
<211> LENGTH: 24
<212> TYPE: DNA
<213> ORGANISM: Artificial sequence
<220> FEATURE:
<223> OTHER INFORMATION: EEF1 qPCR oligo - sense

<400> SEQUENCE: 36
gccccaggac acagagactt tatc 24

<210> SEQ ID NO 37
<211> LENGTH: 22
<212> TYPE: DNA
<213> ORGANISM: Artificial sequence
<220> FEATURE:
<223> OTHER INFORMATION: EEF1 qPCR oligo - antisense

<400> SEQUENCE: 37
caacaccagc agcaacaatc ag 22

<210> SEQ ID NO 38
<211> LENGTH: 19
<212> TYPE: DNA
<213> ORGANISM: Artificial sequence
<220> FEATURE:
<223> OTHER INFORMATION: ABL2 qPCR oligo - sense

<400> SEQUENCE: 38
ttcctggtgc gagaaagtg 19

<210> SEQ ID NO 39
<211> LENGTH: 20
<212> TYPE: DNA
<213> ORGANISM: Artificial sequence -continued
<220> FEATURE:
<223> OTHER INFORMATION: ABL2 qPCR oligo - antisense

<400> SEQUENCE: 39
tacacttggg tgctgggtag 20

<210> SEQ ID NO 40
<211> LENGTH: 20
<212> TYPE: DNA
<213> ORGANISM: Artificial sequence
<220> FEATURE:
<223> OTHER INFORMATION: LAMB3 qPCR oligo - sense

<400> SEQUENCE: 40
actatgctgt gtcccagctc 20

<210> SEQ ID NO 41
<211> LENGTH: 18
<212> TYPE: DNA
<213> ORGANISM: Artificial sequence
<220> FEATURE:
<223> OTHER INFORMATION: LAMB3 qPCR oligo - antisense

<400> SEQUENCE: 41
acagcgctca caatttgg 18

<210> SEQ ID NO 42
<211> LENGTH: 20
<212> TYPE: DNA
<213> ORGANISM: Artificial sequence
<220> FEATURE:
<223> OTHER INFORMATION: LAMC2 qPCR oligo - sense

<400> SEQUENCE: 42
ctgcgagaag tgcaagaatg 20

<210> SEQ ID NO 43
<211> LENGTH: 19
<212> TYPE: DNA
<213> ORGANISM: Artificial sequence
<220> FEATURE:
<223> OTHER INFORMATION: LAMC2 qPCR oligo - antisense

<400> SEQUENCE: 43
atccgtgagc atgtggaag 19

<210> SEQ ID NO 44
<211> LENGTH: 20
<212> TYPE: DNA
<213> ORGANISM: Artificial sequence
<220> FEATURE:
<223> OTHER INFORMATION: PCDH10 qPCR oligo - sense

<400> SEQUENCE: 44
ctaaacacca gcgagcagag 20

<210> SEQ ID NO 45
<211> LENGTH: 20
<212> TYPE: DNA
<213> ORGANISM: Artificial sequence
<220> FEATURE:
<223> OTHER INFORMATION: PCDH10 qPCR oligo - antisense

<400> SEQUENCE: 45
tgtctccatg accactgtcc 20

<210> SEQ ID NO 46
<211> LENGTH: 20
<212> TYPE: DNA
<213> ORGANISM: Artificial sequence
<220> FEATURE:
<223> OTHER INFORMATION: PCDHB5 qPCR oligo - sense

<400> SEQUENCE: 46
ggtggatgtg aatgacaacg 20

<210> SEQ ID NO 47
<211> LENGTH: 20
<212> TYPE: DNA
<213> ORGANISM: Artificial sequence
<220> FEATURE:
<223> OTHER INFORMATION: PCDHB5 qPCR oligo - antisense

<400> SEQUENCE: 47
gaaaggggag atcattctgg 20

<210> SEQ ID NO 48
<211> LENGTH: 19
<212> TYPE: DNA
<213> ORGANISM: Artificial sequence
<220> FEATURE:
<223> OTHER INFORMATION: JAM2 qPCR oligo - sense

<400> SEQUENCE: 48
aggcctatgg gttttctgc 19

<210> SEQ ID NO 49
<211> LENGTH: 19
<212> TYPE: DNA
<213> ORGANISM: Artificial sequence
<220> FEATURE:
<223> OTHER INFORMATION: JAM2 qPCR oligo - antisense

<400> SEQUENCE: 49
ctccgaccca gtttcttcc 19

<210> SEQ ID NO 50
<211> LENGTH: 22
<212> TYPE: DNA
<213> ORGANISM: Artificial sequence
<220> FEATURE:
<223> OTHER INFORMATION: HOXD12 qPCR oligo - sense

<400> SEQUENCE: 50
ctcaacttga acatgacagt gc 22

<210> SEQ ID NO 51
<211> LENGTH: 20
<212> TYPE: DNA
<213> ORGANISM: Artificial sequence
<220> FEATURE:
<223> OTHER INFORMATION: HOXD12 qPCR oligo - antisense

<400> SEQUENCE: 51
aatctgctgc ttcgtgtagg 20

<210> SEQ ID NO 52
<211> LENGTH: 20
<212> TYPE: DNA
<213> ORGANISM: Artificial sequence
<220> FEATURE:
<223> OTHER INFORMATION: HOXD13 qPCR oligo - sense -continued

```
<400> SEQUENCE: 52

tggaacagcc aggtgtactg                                                20


<210> SEQ ID NO 53
<211> LENGTH: 20
<212> TYPE: DNA
<213> ORGANISM: Artificial sequence
<220> FEATURE:
<223> OTHER INFORMATION: HOXD13 qPCR oligo - antisense

<400> SEQUENCE: 53

agctgcagtt tggtgtaagg                                                20


<210> SEQ ID NO 54
<211> LENGTH: 22
<212> TYPE: DNA
<213> ORGANISM: Artificial sequence
<220> FEATURE:
<223> OTHER INFORMATION: ALDH1A1 qPCR oligo - sense

<400> SEQUENCE: 54

tcccgttggt tatgctcatt tg                                             22


<210> SEQ ID NO 55
<211> LENGTH: 23
<212> TYPE: DNA
<213> ORGANISM: Artificial sequence
<220> FEATURE:
<223> OTHER INFORMATION: ALDH1A1 qPCR oligo - antisense

<400> SEQUENCE: 55

ggagtttgct ctgctggttt gac                                            23
```

INHIBITION OF LNCRNA HOTAIR AND RELATED MATERIALS AND METHODS

CROSS-REFERENCE TO RELATED APPLICATIONS

This application is the U.S. National Stage Application of International Patent Application No. PCT/2016/033611, filed May 20, 2016, which claims the benefit of U.S. Provisional Patent Application Nos. 62/164,296, filed May 20, 2015, and 62/298,902, filed Feb. 23, 2016, the disclosures of each of which are incorporated herein by reference in their entireties for all purposes.

STATEMENT REGARDING FEDERALLY SPONSORED RESEARCH

This invention was made with government support under CA113001 awarded by The National Institutes of Health. The government has certain rights in the invention.

SEQUENCE LISTING

The instant application contains a Sequence Listing which has been submitted via EFS-web and is hereby incorporated by reference in its entirety. The ASCII copy, created on Apr. 20, 2016, is named IURTC-2015-175-WO-E_Seq-Listing_ST25, and is 11,792 bytes in size.

FIELD

Embodiments herein provide compositions, methods, and uses for treating a condition characterized by overexpression of long non-coding RNA HOTAIR. In certain embodiments, synthetic polynucleotide analogs capable of hybridizing with a target sequence domain of HOTAIR and inhibiting binding between HOTAIR and PRC2 are provided. In some embodiments, the synthetic polynucleotide analogs can be formulated into a pharmaceutical composition for treating a subject having or at risk of having a condition characterized by HOTAIR overexpression. In certain embodiments, the pharmaceutical composition can resensitize a subject to a chemotherapeutic agent. Other embodiments concern uses for HOTAIR-targeting synthetic polynucleotide analogs, including methods for determining HOTAIR expression in a sample.

BACKGROUND

A very small portion of transcripts in the human genome are associated with protein-coding genes. The majority, an estimated 98%, of human genomic DNA is non-protein coding. Long non-coding RNA (lncRNAs) are non-protein coding transcripts greater than 200 nucleotides in length, distinguishing them from small regulatory RNAs, which include microRNAs and short interfering RNAs, among others. lncRNAs are widely transcribed, and their role in gene expression regulation and disease are gaining increased attention, particularly for their role in carcinogenesis and metastasis of various cancers.

Identified in 2007, HOX antisense intergenic RNA (HOTAIR) is found on chromosome 12q13.13, and has been shown to regulate the HOX genes. Although located in a regulatory boundary in the HOXC cluster, knockdown of HOTAIR did not affect expression of the HOXC cluster, but rather led to depression of a 40-kb region of the HOXD cluster. HOTAIR is a spliced and polyadenylated RNA of 2,158 nucleotides and 6 exons.

HOTAIR is a trans-acting lncRNA that interacts with Polycomb Repressive Complex 2 (PRC2), and is necessary for PRC2 occupancy at specific loci, trimethylation of histone H3 lysine K27 (H3K27me3) by enhancer of zeste 2 (EZH2), and subsequent gene repression. PRC2 is a histone methyltransferase that implements epigenetic silencing during different processes, including cancer development and progression. PRC2 comprises EZH2, SUZ12, and EED subunits. While EZH2 is the key subunit involved in the methyltransfer process, the other subunits are required to regulate EZH2 catalytic activity. For example, EED regulates EZH2's affinity to RNA, thereby increasing the specificity of PRC2 function. HOTAIR functions as a molecular scaffold, and interacts not only with PRC2, but also with the LSD1 complex to regulate gene expression. LSD1 is involved in demethylation of histone H3 at lysine 4. Specifically, PRC2 binds to a 5' domain of HOTAIR, while LSD1 binds to a 3' domain. HOTAIR coordinates the chromatin modification function of each of these complexes, thereby altering expression of genes involved in various cellular functions.

HOTAIR has been demonstrated to play a key role in the initiation, progression, and metastasis of many different types of cancer, including ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma and pancreatic cancer. HOTAIR has also been shown to be a regulator of rheumatoid arthritis.

SUMMARY

Embodiments disclosed herein concern compositions and methods for treating a condition characterized by overexpression of long non-coding RNA HOTAIR. In certain embodiments, synthetic polynucleotide analogs capable of hybridizing with a target sequence domain of HOTAIR are provided. The synthetic polynucleotide analogs can be formulated into a pharmaceutical composition for treating a subject having or at risk of having a condition characterized by HOTAIR overexpression. In certain embodiments, the pharmaceutical composition can resensitize a subject to a chemotherapeutic agent. Other embodiments concern uses for HOTAIR-targeting synthetic polynucleotide analogs, including methods for determining HOTAIR expression in a sample.

Certain embodiments provide a synthetic polynucleotide analog that hybridizes to a target sequence in the 89-mer minimum interacting region of HOX antisense intergenic RNA (HOTAIR), thereby inhibiting binding of HOTAIR to Polycomb Repressive Complex 2 (PRC2). In certain embodiments, the nucleotide sequence capable of hybridizing to the target sequence is 5 to 20 nucleic acids in length. In some embodiments, the nucleotide sequence capable of hybridizing to the target sequence is the reverse complement of the target sequence. The synthetic polynucleotide analog can be, for example, a peptide nucleic acid, a locked nucleic acid, a morpholino, a bridged nucleic acid, a phosophorothioate oligonucleotide, or a 2'-O-methyl-substituted RNA.

In certain embodiments described herein, the nucleotide sequence of the synthetic polynucleotide analog capable of hybridizing to the target sequence includes at least five contiguous nucleic acid sequences from the nucleic acid sequence of SEQ ID NO: 14. In a particular embodiment, the nucleotide sequence includes all of SEQ ID NO:14.

In other embodiments, the synthetic polynucleotide analog capable of targeting a target sequence of HOTAIR is a peptide nucleic acid or a peptide nucleic acid derivative.

In certain embodiments, the synthetic polynucleotide analog is conjugated to at least one other polypeptide, such as a cell penetrating peptide, a cell targeting peptide, or a ph Low Insertion Peptide (pHLIP). In a particular embodiment, the synthetic polynucleotide analog is conjugated to a pHLIP that includes a nucleotide sequence of SEQ ID NO: 18.

Other embodiments described herein provide pharmaceutical compositions that include a synthetic polynucleotide analog described herein and a pharmaceutically acceptable carrier. In certain embodiments, the pharmaceutical composition can further include a pharmaceutically acceptable excipient, delivery vehicle, or both. In certain embodiments, the pharmaceutical composition includes a liposome formulation. In some embodiments, the pharmaceutical composition includes at least one chemotherapeutic agent, such as platinum containing chemotherapeutic agents (e.g., cisplatin carboplatin; oxaliplatin; nedaplating; triplatin tetranitrate; phenanthriplatin; picoplatin; satraplatin) and topoisomerase inhibitors (e.g., etoposide; amsacrine; teniposide; and doxorubicin).

Yet other embodiments provide methods for treating a subject having a condition characterized by overexpression of HOTAIR, the method including administering to the subject a therapeutically effective amount of a pharmaceutical composition described herein. In certain embodiments, such method can be used to treat ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma, pancreatic cancer, or rheumatoid arthritis. In certain embodiments where the condition to be treated is a cancer, the methods can further include administering at least one traditional chemotherapeutic agent to the subject.

In certain embodiments provided herein, a cell is resensitized to a chemotherapeutic agent by contacting a chemotherapeutic resistant cell with an effective amount of a synthetic polynucleotide analog provided herein. In certain embodiments, these resensitization methods can be carried out in vivo or in vitro. In certain embodiments, the method for resensitizing a cell to a chemotherapeutic agent is performed in a subject having a cancer that is resistant to the chemotherapeutic agent, thereby resensitizing the cancer to the chemotherapeutic agent.

Yet other embodiments provide compositions provide synthetic polynucleotides analogs that include the nucleotide sequence of SEQ ID NO: 14, the synthetic polynucleotide being conjugated to one or more fluorescent molecules or fluorophores, such as fluorescein, green fluorescent protein, rhodamine, cyanine dyes, and Alexa dyes. Other embodiments provide methods of use for such compositions, including determining HOTAIR expression levels in a test sample, determining intracellular expression location of HOTAIR, and diagnosing a subject as having a condition characterized by overexpression of HOTAIR, or determining a subject as being at risk of having a condition characterized by overexpression of HOTAIR.

Other embodiments provide a method for isolating and identifying at least one HOTAIR binding partner, where such binding partners are immunoprecipitated from a sample using a synthetic polynucleotide analog described herein. In some embodiments, the synthetic polynucleotide includes a nucleic acid having the sequence of SEQ ID NO: 14.

BRIEF DESCRIPTION OF THE DRAWINGS

The patent or application file contains one or more drawings executed in color and/or one or more photographs.

FIG. 1 shows the sequence and structure of the structured 89-mer minimum interacting region of HOTAIR (SEQ ID NO: 1), target sequences for the five PNAs (SEQ ID NOs: 2-6), the RNA to DNA sequences for the target sequences (SEQ ID NOs: 7-11), and the sequences of the five PNAs (SEQ ID NOs: 12-16). SEQ ID NOs are provided in order of appearance.

FIGS. 5F-FG are bar graphs showing the change in expression for the noted HOTAIR targets following treatment with either PNA2 or control PNA.

DETAILED DESCRIPTION

Figure 2A:
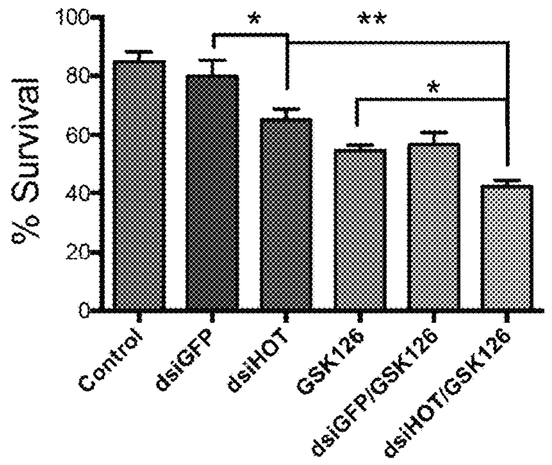
FIG. 2A is a bar graph showing cell survival following noted treatments to inhibit HOTAIR and/or inhibit EZH2. Asterisks indicate P<0.05 (*) or P<0.01 (**).

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Embodiments disclosed herein concern compositions and methods for treating a condition characterized by overexpression of long non-coding RNA HOTAIR. In certain embodiments, synthetic polynucleotide analogs capable of hybridizing with a target sequence domain of HOTAIR are provided. The synthetic polynucleotide analogs can be formulated into a pharmaceutical composition for treating a subject having or at risk of having a condition characterized by HOTAIR overexpression. In certain embodiments, the pharmaceutical composition can resensitize a subject to a chemotherapeutic agent. Other embodiments concern uses for HOTAIR-targeting synthetic polynucleotide analogs, including methods for determining HOTAIR expression in a sample and methods for diagnosing a subject as having a condition or at risk of having a condition characterized by HOTAIR overexpression.

Definitions

So that the present disclosure may be more readily understood, certain terms are first defined. Terms that are not otherwise defined herein are used in accordance with their plain and ordinary meaning.

It is to be understood that the terminology and phraseology employed herein are for the purpose of description and should not be regarded as limiting.

"Nucleotide" can refer to the monomer units that are assembled to form a polynucleotide. This definition includes the nucleotide monomers used to form peptide nucleic acids (PNAs) and other synthetic polynucleotide analogs described herein.

"Polynucleotide" can refer to a polymer composed of nucleotides (ribonucleotides, deoxyribonucleotides, related naturally occurring structural variants, and synthetic non-naturally occurring analogs thereof, e.g., PNAs) linked via phosphodiester bonds, related naturally occurring structural variants and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide nucleic acids (PNAs), and the like.

"Peptide nucleic acid," or "PNA" can refer to a DNA analog in which the phosphate backbone has been replaced by (2-aminoethyl) glycine carboyl units that are linked to the nucleotide bases by the glycine amino nitrogen and methylene carbonyl linkers. The backbone is thus composed of peptide bonds linking the nucleobases. Because the PNA backbone is composed of peptide linkages, the PNA is typically referred to as having an amino-terminal and a carboxy-terminal end. However, a PNA can be also referred to as having a 5' and a 3' end in the conventional sense, with reference to the complementary nucleic acid sequence to which it specifically hybridizes. The sequence of a PNA molecule is described in conventional fashion as having nucleotides G, U, T, A, and C that correspond to the nucleotide sequence of the PNA molecule. Such polynucleotides can be synthesized, for example, using an automated DNA synthesizer. Typically, PNAs are synthesized using either Boc or Fmoc chemistry. PNAs and other polynucleotides can be chemically derivatized by methods known to those skilled in the art. For example, PNAs have amino and carboxy groups at the 5' and 3' ends, respectively, that can be further derivatized. Custom PNAs can also be synthesized and purchased commercially.

As used herein, "subject" can refer an individual having a condition, suspected of having a condition, or at risk of having a condition characterized by HOTAIR overexpression. As used herein "characterized by HOTAIR expression" refers to any condition wherein HOTAIR has been shown to be overexpressed relative to a subject free of the condition. Known conditions characterized by HOTAIR overexpression include but are not limited to ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma, pancreatic cancer, and rheumatoid arthritis. A subject can be any individual suffering from a condition characterized by HOTAIR overexpression, including but not limited to human, canine, rodent, primate, swine, equine, sheep, and feline. In certain embodiments, the subject is a human.

As used herein, the term "pharmaceutical composition" encompasses a product comprising one or more active ingredients, and an optional carrier, delivery vehicle, or excipient comprising inert ingredients, as well as any product that results, directly or indirectly, from combination, complexation, or aggregation of any two or more of the ingredients, or from dissociation of one or more of the ingredients, or from other types of reactions or interactions of one or more of the ingredients. The composition is especially suitable for therapeutic use. Generally, pharmaceutical compositions are prepared by uniformly and intimately bringing the active ingredient into association with a liquid carrier, vehicle, or excipient, or a finely divided solid carrier, vehicle, or excipient, or both, and then, if necessary, shaping the product into the desired formulation. The pharmaceutical composition includes enough of the active ingredient to produce the desired effect. Accordingly, the pharmaceutical compositions described herein encompass any composition made by admixing a compound or PNA described herein and a pharmaceutically acceptable carrier, vehicle, or excipient.

The terms "pharmaceutically acceptable" or "pharmacologically acceptable" as used herein refer to the carrier, delivery vehicle, or excipient being compatible with the other composition ingredient, as well as to compositions that do not substantially produce adverse reactions, e.g., toxic, allergic, or immunological reactions, when administered to a subject.

As used herein, the term "treating" includes reducing or alleviating at least one adverse effect or symptom of a condition or disorder through introducing in any way a therapeutic composition of the present disclosure into the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective amount" refers to a dose of a therapeutic agent sufficient to bring about a beneficial or desired clinical effect. Said dose can be administered in one or more administrations. However, the precise determination of what would be considered an effective dose may be based on factors individual to each subject, including, but not limited to, the patient's age, size, type or extent of condition, stage of the condition, route of administration, the type or extent of supplemental therapy used (e.g., chemotherapy), ongoing condition process, and type of treatment desired (e.g., aggressive versus conventional treatment).

As used herein, the term "sample" is used in its broadest sense. In one sense, it is meant to include a specimen or culture obtained from any source, as well as biological samples. Biological samples may be obtained from subjects, and encompass fluids, solids, tissues, and gases. In certain embodiments, biological samples obtained from subjects are cells isolated from tissue or tumor biopsies. Samples also include cells of immortalized cells cultures, including but not limited to ovarian cancer cell lines A2780p, A2780_CR5, and Kuramochi, and breast cancer cell lines MCF-7, MDA-MB231, and SKBR3. Cell lines representative of other conditions characterized by overexpression of HOTAIR can also be a sample.

Synthetic Polynucleotide Analogs

Certain embodiments described herein provide synthetic polynucleotide analogs capable of hybridizing to HOX antisense intergenic RNA (HOTAIR). In some embodiments, the synthetic polynucleotide analogs can be single stranded. Binding of a synthetic polynucleotide analog described herein to HOTAIR can inhibit or prevent HOTAIR's interaction with Polycomb Repressive Complex 2 (PRC2). HOTAIR has been shown to be necessary for PRC2 occupancy and histone H3 lysine-27 trimethylation of various genes located on different chromosomes. PRC2 is a histone methyltransferase that implements epigenetic silencing during different processes, including cancer development and progression.

In certain embodiments, the synthetic polynucleotide analogs mimic single-stranded oligonucleotide in their ability to hybridize to HOTAIR. Synthetic polynucleotide analogs include peptide nucleic acids (PNAs) and locked nucleic acids (LNAs). Both PNAs and LNAs have both high affinity and sensitivity for natural polynucleotides. Other synthetic polynucleotide analogs contemplated herein include morpholinos, bridged nucleic acids (BNAs), phosophorothioate oligonucleotides, and 2'-O-methyl-substituted RNA, although other synthetic polynucleotide analogs can also be used.

In some embodiments, the synthetic polynucleotide analogs can be LNAs. LNA polynucleotides are modified RNA nucleotides. The ribose moiety of an LNA polynucleotide is modified with an extra bridge connecting the 2' and 4' carbons. The bridge "locks" the ribose the 3'-endo structural conformation, which is often found in the A-form of DNA or RNA. The locked ribose conformation enhances base stacking and backbone pre-organization. This significantly increases the thermal stability (melting temperature) of oligonucleotides. Due to their constrained backbone, LNA polynucleotides have a high affinity for single-stranded DNA or RNA. LNA bases can be included in an LNA backbone, 2'-O-methyl RNA backbone, 2'-methoxyethyl RNA backbone, 2'-fluoro RNA DNA backbone, or a DNA backbone. LNA polynucleotides can utilize either a phosphodiester or phosphorothioate backbone. In addition to high affinity, LNA polynucleotides display high in vivo stability and slower renal clearance.

In other embodiments, the synthetic polynucleotide analog can be a BNA polynucleotide. BNA monomers can contain a five-, six-, or even a seven-membered bridged structure with a fixed C3'-endo sugar puckering. The bridge is synthetically incorporated at the 2', 4'-position of the ribose to afford a 2', 4'-BNA monomer. An increased conformational inflexibility of the sugar moiety in BNA oligonucleotides results in a gain of high binding affinity with complementary single-stranded RNA and/or double-stranded DNA. BNAs are useful for the detection of short DNA and RNA targets, are capable of single nucleotide discrimination, and are resistant to exo- and endonucleases, resulting in high stability for in vivo and in vitro applications.

In yet other embodiments, the synthetic polynucleotide analog can be a phosphorothioate (PS) polynucleotide. In a PS backbone, a sulfur atom replaces one non-bridging oxygen atom and increases nuclease resistance.

In certain embodiments, the synthetic polynucleotide analog can be a 2'-O-methyl polynucleotide. In a 2'-O-methyl polynucleotide, a methyl group replaces a hydrogen atom in the 2'-hydroxyl group in the ribose ring of RNA, imparting nuclease resistance and inhibiting RNAse-H activation, leaving target RNA intact. Although the 2'-O-methyl modification is insensitive to endonucleases, it is still partially susceptible to exonuclease degradation. By combining PS linkages and 2'-O-methyl nucleotides, much greater in vivo stability can be achieved.

In some embodiments, the synthetic polynucleotide analog can be a peptide nucleic acid (PNA) polynucleotide. A PNA polynucleotide is a polypeptide with N-(2-aminoethyl) glycine as the unit backbone. Like DNA and RNA, PNA also selectively binds to complementary nucleic acid. Having a neutral backbone due to the replacement of the phosphates in the backbone, the binding between PNA and RNA is stronger than that between DNA and RNA or RNA and RNA due to the lack of electrostatic repulsion. The neutral backbone also results in the binding being practically independent of salt concentration. In addition to having increased binding affinity, PNAs are known to bind RNA with increased specificity, with sensitivities capable of discriminating against a single base pair mismatch. This is a significant improvement over strategies such as RNAi utilizing siRNA or miRNA. Since PNA is structurally markedly different from DNA, PNA is very resistant to both proteases and nucleases, and is not recognized by the hepatic transporter(s) recognizing DNA.

HOTAIR-Targeting Synthetic Polynucleotide Analogs

Figure 3A:
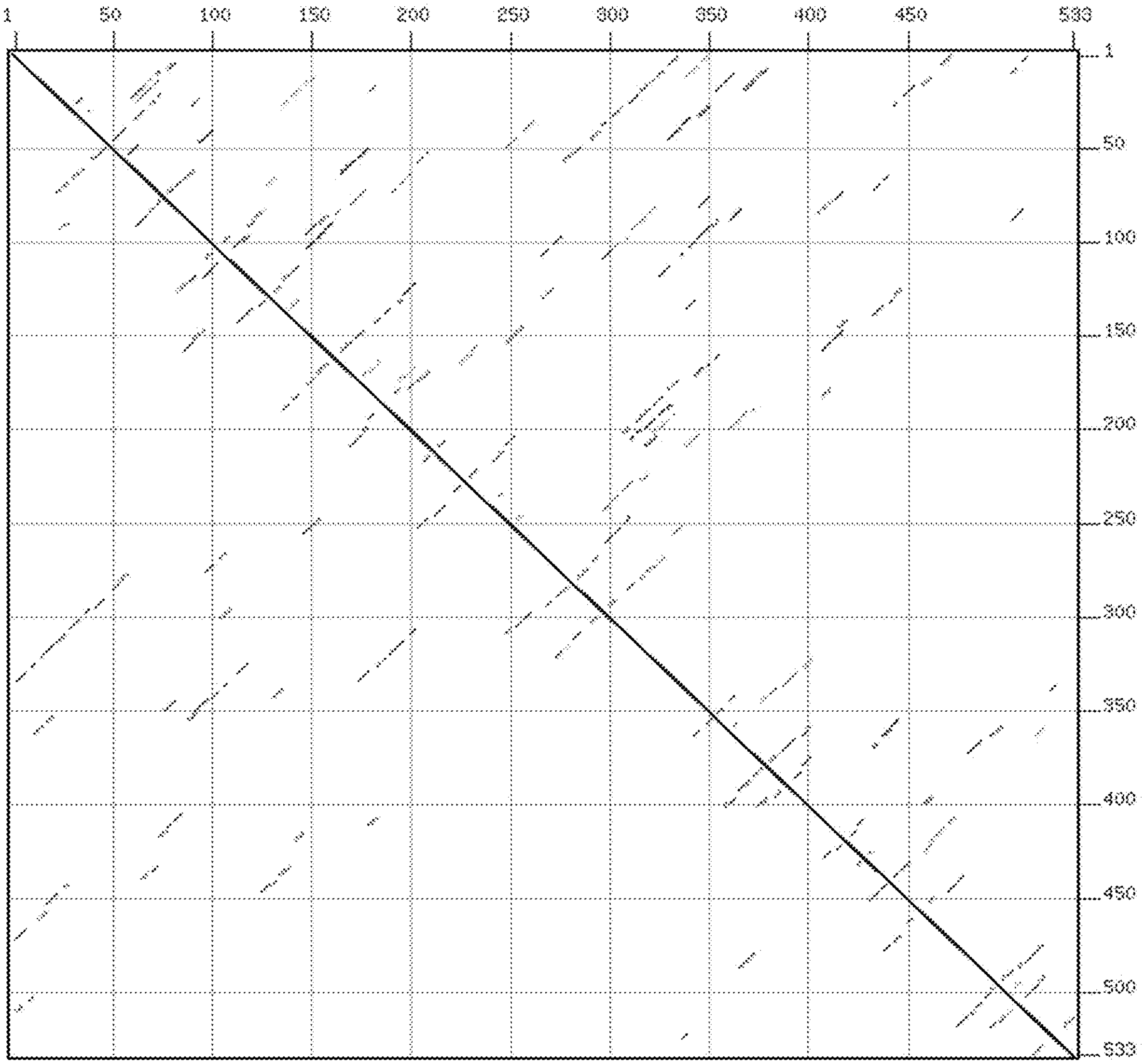
FIG. 3A shows mFold results indicating that the secondary structure of the structured 89-mer minimum interacting region forms a single stranded region having the structure shown in FIG. 3B.
Figure 3B:
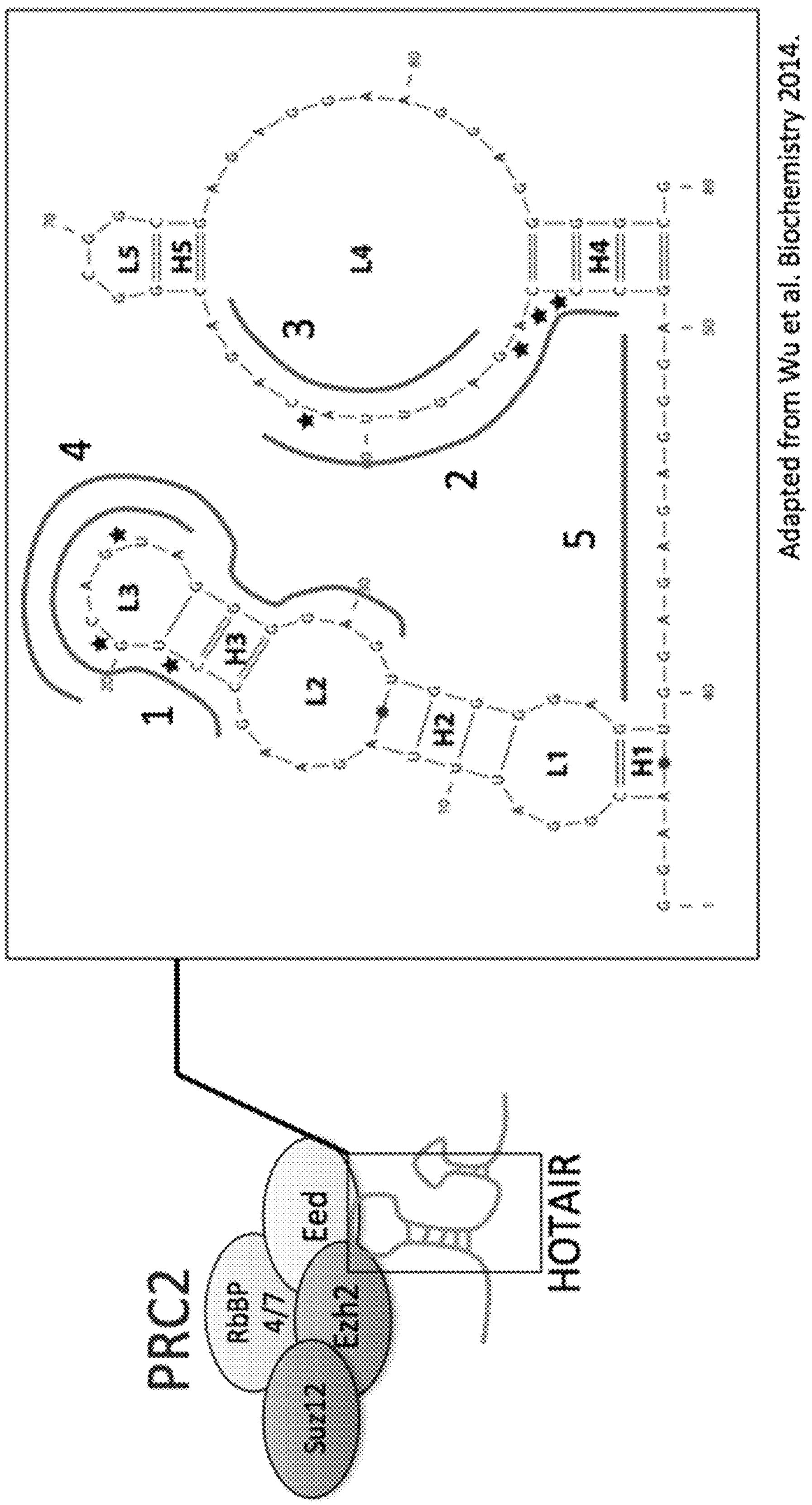
FIG. 3B is a schematic showing the HOTAIR/PRC2 complex (left) and the structured 89-mer minimum interacting region (SEQ ID NO: 1), including target sequence domains 1 through 5.

In certain embodiments, a synthetic polynucleotide analog provided herein is an antisense synthetic polynucleotide analog capable of targeting and hybridizing with the structured 89-mer minimum interacting region of HOTAIR, or a portion thereof (see FIGS. 1 and 3B; SEQ ID NO: 1). Synthetic polynucleotide analogs can be complementary to one of several segments, or target domains, of HOTAIR's single-stranded regions, as shown in FIGS. 1 and 3B. In some embodiments the target domain can be a short RNA sequence that is a partial sequence of the entire structured 89-mer minimum interacting region of HOTAIR. In certain embodiments, hybridization of a synthetic polynucleotide analog to a target domain can prevent the interaction of PRC2 with HOTAIR.

In certain embodiments, the target domain, and thus the antisense (complementary) synthetic polynucleotide analog, can be about 5 to about 20 nucleotides in length. The length of the synthetic polynucleotide analog can be optimized for the specific intended use and target domain. In some embodiments, the target domain and its complementary synthetic polynucleotide can have a length of 10 to 15 nucleotides. In other embodiments, the target domain and its complementary synthetic polynucleotide can have a length of 10 to 12 nucleotides. In a particular embodiment, the target domain and its complementary synthetic polynucleotide can have a length of 10 nucleotides.

In some embodiments, the short RNA target sequence can be, for example, 5'-GCCUGCAGUA-3' (target 1; SEQ ID NO: 2), 5'-CCCAGAGUUAC-3' (target 2; SEQ ID NO: 3), 5'-GAGUUACAGA-3' (target 3; SEQ ID NO: 4), 5'-GCA-GUAGGGGAG-3' (target 4; SEQ ID NO: 5), or 5'-GGA-GAGAGGG-3' (target 5; SEQ ID NO: 6). In certain embodiments, the antisense synthetic polynucleotide can have a nucleic acid sequence of 5'-TACTGCAGGC-3' (antisense sequence 1; SEQ ID NO: 12), 5'-GTAACTCTGGG-3' (antisense sequence 2; SEQ ID NO: 13), 5'-TCTGTAACTC-3' (antisense sequence 3; SEQ ID NO: 14), 5'-CTC-CCCTACTGC-3' (antisense sequence 4; SEQ ID NO: 15), 5'-CCCTCTCTCC-3' (antisense sequence 5; SEQ ID NO: 16). These examples are presented in FIG. 3B, which shows the location of targets 1-5 on the structured 89-mer minimum interacting region of HOTAIR in a schematic alignment with numbered segments representing antisense sequences 1-5.

In certain embodiments, the antisense synthetic polynucleotide can be a peptide nucleic acid (PNA).

In other embodiments, the antisense synthetic polynucleotide analog can have a nucleic acid sequence that includes at least five contiguous nucleic acids of the nucleic acid sequence of SEQ ID NO: 14. Therefore, in some embodiments, the synthetic polynucleotide analog can be a partial sequence of SEQ ID NO: 14. In other embodiments, the synthetic polynucleotide analog can include a partial sequence or a full sequence of SEQ ID NO: 14, and can further include one or more additional nucleic acids. In embodiments where the synthetic polynucleotide analog includes one or more additional nucleic acids, the one or more additional nucleic acids can have or result in a sequence that is divergent from the nucleic acid sequence of SEQ ID NO: 14. In certain embodiments, the one or more additional nucleic acids forms an extension end.

Figure 2B:
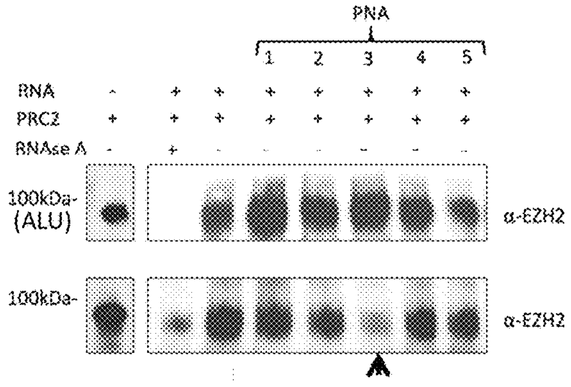
FIG. 2B shows the results of a pull-down assay, where HOTAIR or ALU (control) RNA were pulled down with streptavidin-coated protein A/G plus agarose beads.

In other embodiments, the target domain can be the short RNA target sequence 5'-GAGUUACAGA-3' (target 3; SEQ ID NO: 4) and the antisense synthetic polynucleotide analog can have a nucleic acid sequence of 5'-TCTGTAACTC-3' (antisense sequence 3; SEQ ID NO: 14). In such an embodiment, antisense sequence 3, being the reverse complement of target 3, hybridizes to the target domain. In a particular embodiment, the antisense synthetic polynucleotide can be a PNA having the nucleic acid sequence of antisense sequence 3. As described herein, PNA3 selectively inhibits the interaction between HOTAIR and PRC2 (FIG. 2B). Throughout the present disclosure, such a PNA will be referred to as PNA3 (PNA having a nucleic acid sequence of antisense sequence 3, SEQ ID NO: 14). Other synthetic polynucleotide analogs are similarly identified herein (e.g., a PNA having the sequence of antisense sequence 1 (SEQ ID NO: 12), which targets a sequence of target 1 (SEQ ID NO: 2), is termed PNA1).

In certain embodiments, a synthetic polynucleotide analog can be covalently coupled to a cell penetrating peptide (CPP). Coupling a CPP to the synthetic polynucleotide analog can improve cytosolic delivery of the synthetic polynucleotide analog. CPPs represent short polypeptide sequences of about 10 to about 30 amino acids which can cross the plasma membrane of mammalian cells. CPPs include, but are not limited to, Tat and Tat-derived peptides, members of the penetratin family, transportans, nuclear localizing signal (NLS), hCT-derived CPPs, polyarginine CPPs, Pep-2, and Pep-3. In other embodiments, synthetic polynucleotide analogs can be formulated in a composition that includes a cell penetrating agent, such as liposomes, which enhance delivery of the synthetic polynucleotide analogs to the intracellular space.

In other embodiments, a synthetic polynucleotide analog can be conjugated to a cell-targeting peptide. Cell targeting peptides are peptides with specific binding activity for a given tissue or cell type, allowing the synthetic polynucleotide analog to be targeted to only certain tissues or cell types. For example, a synthetic polynucleotide analog can be selectively targeted to a tumor microenvironment or to cancerous cells overexpressing HOTAIR.

Figure 12A:
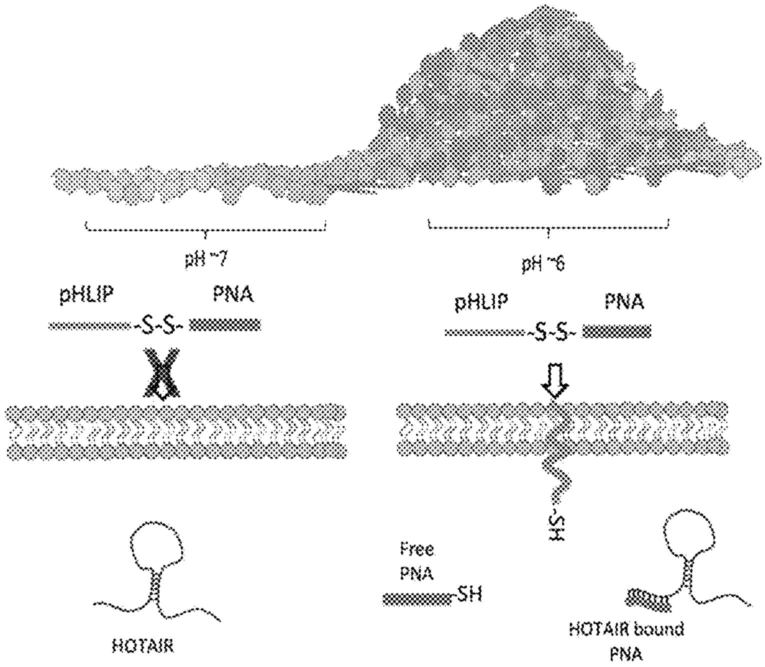
FIG. 12A is a diagram illustrating the mechanism for pHLIP-PNA mediated targeting of lncRNA HOTAIR.
Figure 12B:
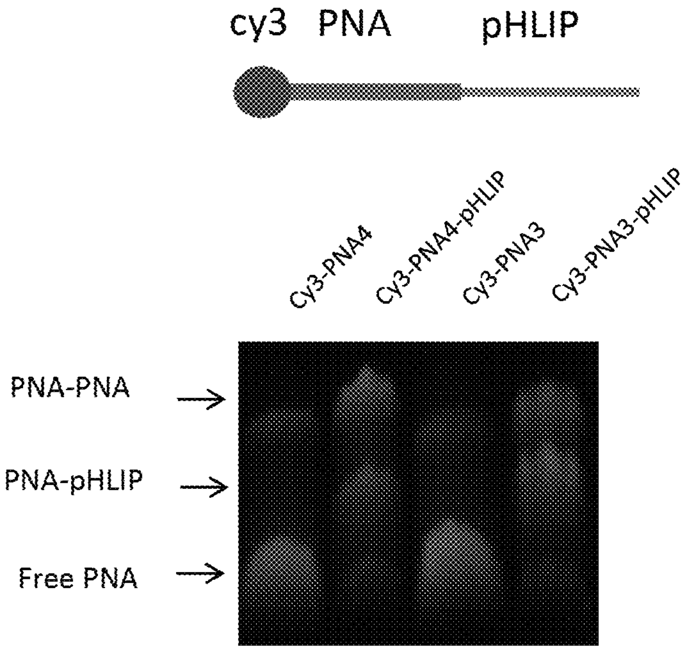
FIG. 12B shows a cartoon of pHLIP-peptide conjugated to cy3 labeled PNA and an image of the cy3 labeled pHLIP-PNA in a 4% TBE-acrylamide gel, along with PNA-PNA and free PNA.

In some embodiments, a HOTAIR-targeting synthetic polynucleotide analog described herein can be conjugated to a pH Low Insertion Peptide (pHLIP) (FIG. 12B). This allows for the selective targeting of the acidic microenvironment (~pH 6) present in many tumors, as pHLIP can only enter the lipid bilayer of a cell under low pH conditions. As depicted in FIG. 12A, pHLIP can enter the lipid bilayer to form a stable transmembrane structure under low pH conditions, with its C-terminus extending into the cell. Following insertion into the bilayer, the disulfide bond between the synthetic polynucleotide analog and pHLIP is cleaved due to the reducing environment found in the cell (FIG. 12A). The freed synthetic polynucleotide analog can then bind to its target (HOTAIR), and inhibit its interaction with the PRC2 complex (FIG. 12A).

A domain of the bacteriorhodopsin protein, pHLIPs are unstructured in neutral and basic pHs, where they can interact with the outer surface of lipids in a reversible manner. However, in acidic environments (pH~6), pHLIPs can form stable transmembrane structures. As many tumors have an acidic microenvironment (pH~6) due to increased lactic acidosis (Warburg effect), HOTAIR-targeting synthetic polynucleotide analogs described herein can be modified to selectively target tumor cells by conjugating the PNA to a pHLIP. This approach prevents the HOTAIR-targeting pHLIP-synthetic polynucleotide analog conjugate from entering non-target cells, improving the efficiency and effectiveness of a HOTAIR-targeting treatment. Tumors capable of being selectively targeted by pHLIP-conjugated HOTAIR-targeting synthetic polynucleotide analogs due to their acidic microenvironments include, but are not limited to, ovarian cancer, bladder cancer, cervical cancer, lung cancer, testicular cancer, lymphomas, and other cancers described herein.

In other embodiments, any known pHLIP capable of carrying a cargo molecule can be used as a delivery molecule for a HOTAIR-targeting synthetic polynucleotide analog described herein. Any of the HOTAIR-targeting synthetic polynucleotide analogs described herein can be conjugated to an appropriate pHLIP. Further description and examples of useful pHLIPs are provided in U.S. Pat. Nos. 8,846,081 and 8,703,909, both of which are expressly incorporated herein by reference in their entirety. In certain embodiments, the pHLIP has a sequence of AAEQNPIYWARYADWLFTTPLLLLDLALLVDADEGTXG (SEQ ID NO: 18), where X can be a cysteine group derivatized with 3-nitro-2-pyridinesulphenyl (NPys). In a particular embodiment, the pHLIP of SEQ ID NO: 18 is conjugated to PNA3 (SEQ ID NO: 14).

Figure 12C:
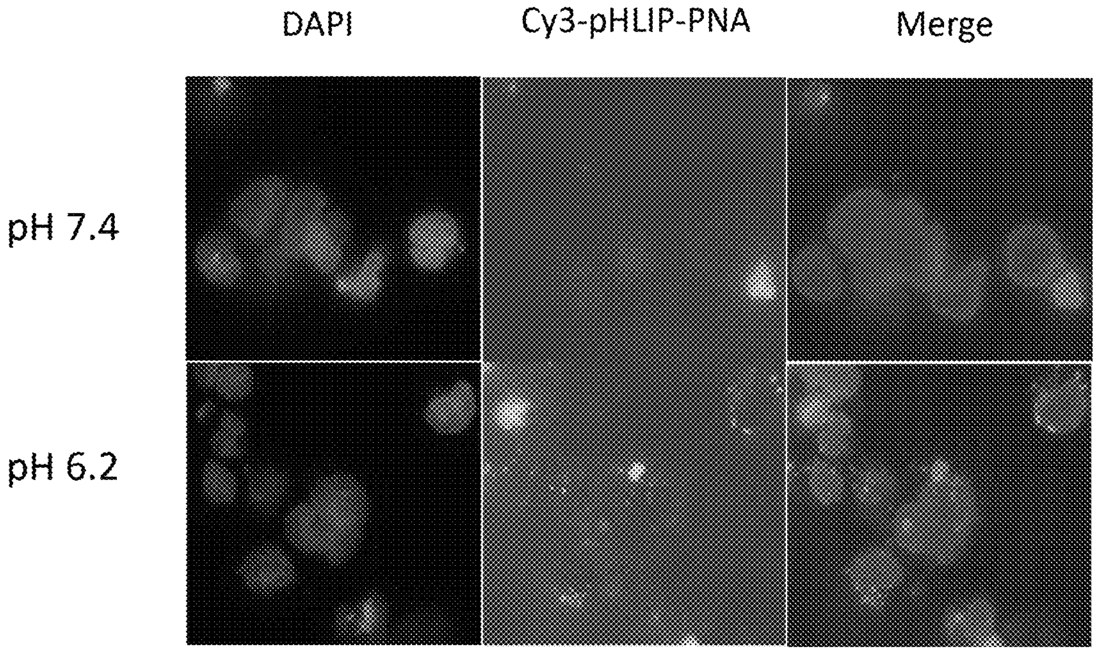
FIG. 12C is series of images showing the effect of pH on the ability of pHLIP-PNA conjugates to enter cells.
Figure 12D:
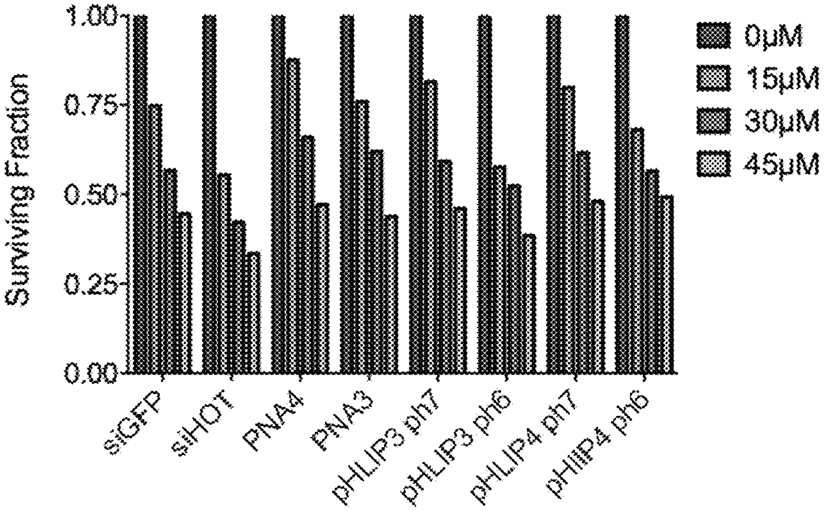
FIG. 12D is a bar graph showing decreased survival of cells treated with pHLIP-PNA3 at pH 6 compared to pHLIP-PNA4 at the same pH.

As illustrated in FIG. 12C, HOTAIR-targeting pHLIP-PNA conjugates are incorporated into cells only at low pH conditions. Under normal pH conditions (pH 7), CDDP resistant A2780_CR5 cells showed similar survival to increasing doses of CDDP relative to the controls (FIG. 12D; see pHLIP-PNA3 vs pHLIP-PNA4). However, at a more acidic pH (~pH 6.2), there was a marked decrease in cell survival with the pHLIP-PNA3 conjugate (HOTAIR specific).

Figure 13A:
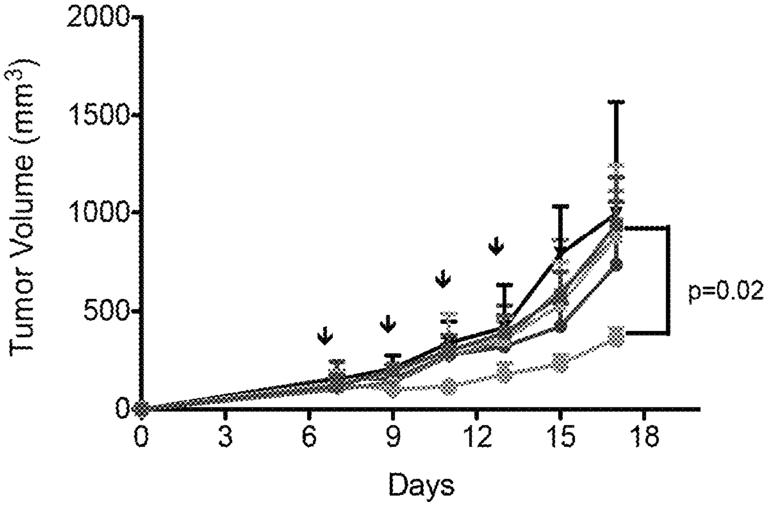
FIG. 13A is a line graph showing reduced tumor volume in mice co-administered pHLIP-PNA3+CDDP compared to pHLIP-control PNA+CDDP. Arrows represent 1 $mgkg^{-1}$ PNA and/or 2 mg $kg^{-1}$ CDDP.
Figure 13B:
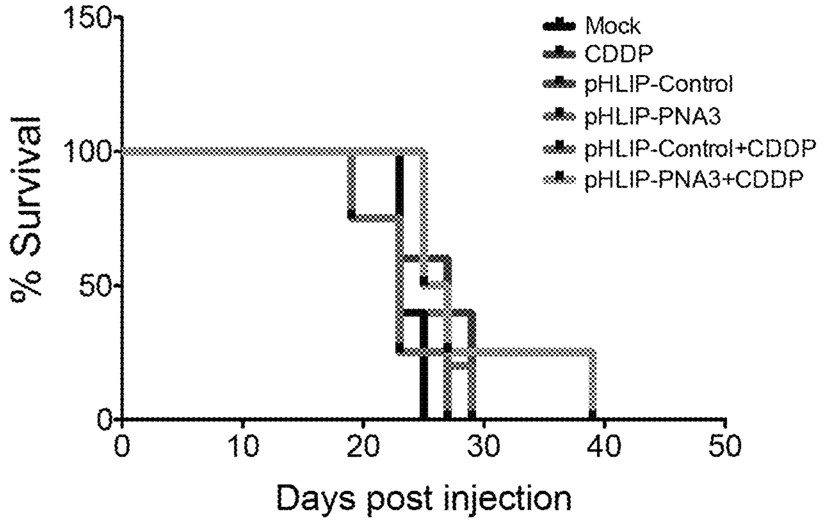
FIG. 13B shows that survival of mice treated with pHLIP-PNA3 was greatly improved compared to mock-treated mice.

In certain exemplary methods, in vivo results from mice engrafted with A2780_CR5 cells further demonstrate the ability of HOTAIR-targeting pHLIP-PNA conjugates to selectively target the acidic microenvironment of tumors. As shown in FIGS. 13A and 13B, treatment with pHLIP-PNA3 and CDDP resulted in a 2-fold reduction in tumor volume compared to mock treatment and increased progression-free survival, respectively.

Any cell-targeting peptide known in the art can be used in an embodiment described herein.

In yet other embodiments, both a CPP and a cell targeting peptide are conjugated to a HOTAIR-targeting synthetic polynucleotide analog.

In certain embodiments, CPP and/or cell targeting peptide can be conjugated to either the 3' or 5' end of the synthetic polynucleotide analog. In certain embodiments, conjugation of a cell-targeting peptide can be facilitated by modifying an amino acid of the cell-targeting peptide. In a particular embodiment, conjugation of a cell-targeting peptide can be facilitated by incorporating a cysteine derivatized with 3-nitro-2-pyridinesulphenly (NPys).

In some embodiments, HOTAIR-targeting synthetic polynucleotide analogs described herein can further comprise a linker. The CPP and/or cell targeting peptide can be conjugated to the synthetic polynucleotide analog via the linker. The linker can also function to improve solubility and help avoid self-aggregation of the synthetic polynucleotide analog. Linkers include, but are not limited to lysine and O-linker.

In other embodiments, a HOTAIR-targeting PNA described herein can be a PNA derivative (e.g., GPNA) wherein the PNA and the PNA derivative have the same binding specificity. PNA derivatives can provide adequate cellular uptake while avoiding the need to conjugate a large accessory peptide, such as a CPP or cell targeting peptide, to the PNA. This can help avoid steric hindrance and electrostatic repulsion resulting from the conjugated peptides, thereby improving the PNAs binding affinity.

In some embodiments, HOTAIR-targeting synthetic polynucleotide analogs described herein can be conjugated to one or more fluorescent molecules or fluorophores. The resulting complex is particularly useful where it is desired to either observe overall HOTAIR expression in a cell or determine the lncRNAs subcellular location. Fluorescent-tagged synthetic polynucleotide analogs can additionally include any of the modifications (e.g., CPP conjugation, cell-targeting peptide conjugation) described herein. In certain embodiments, the fluorescent-tagged synthetic polynucleotide analog does not include any modification. The fluorescent-tagged synthetic polynucleotide analog can be introduced to a cell using a CPP, or via microinjection or electroporation, thereby avoiding steric hindrance or electrostatic repulsive forces resulting from conjugation of the synthetic polynucleotide analog to an additional peptide. Fluorescent molecules and fluorophores can be any fluorescent molecule or fluorophores known to those of skill in the art for tagging polynucleotides. Fluorescent molecules can include, but are not limited to fluorescein, green fluorescent protein, rhodamine, cyanine dyes, and Alexa dyes. In certain embodiments, the HOTAIR-targeting synthetic polynucleotide analog conjugated to a fluorescent molecule of fluorophore can be formulated into a composition along with a suitable carrier. A suitable carrier can be, for example, a diluent such as saline and other aqueous buffer solutions.

Pharmaceutical Compositions

Embodiments herein provide for administration of HOTAIR-targeting synthetic polynucleotide analogs in a biologically compatible form suitable for pharmaceutical administration in vivo. By "biologically compatible form suitable for administration in vivo" is meant a form of the active agent (e.g. HOTAIR-targeting synthetic polynucleotide analog of the embodiments) to be administered in which any toxic effects are outweighed by the therapeutic effects of the active agent. Administration of a therapeutically active amount of the therapeutic compositions is defined as an amount effective, at dosages and for periods of time necessary to achieve a desired result. For example, a therapeutically active amount of a compound may vary according to factors such as the disease state, age, sex, and weight of the individual, and the ability of formulations to elicit a desired response in the individual. Dosage regimens may be adjusted to provide the optimum therapeutic response.

In certain embodiments, a pharmaceutical composition including a HOTAIR-targeting synthetic polynucleotide can further include one or more chemotherapeutic agents. In certain embodiments, the chemotherapeutic agent can be a platinum-containing chemotherapeutic, such as cisplatin, carboplatin, oxaliplatin, nedaplating, triplatin tetranitrate, phenanthriplatin, picoplatin, and satraplatin. In other embodiments, the chemotherapeutic agent can be a topoisomerase inhibitor, such as etoposide, amsacrine, teniposide, and doxorubicin. In some embodiments, the chemotherapeutic agent can be cisplatin or etoposide, or both cisplatin and etoposide.

In some embodiments, a pharmaceutical composition disclosed herein can be administered by any mode known to work for such a compositions, including, but not limited to, subcutaneous, intravenous, by oral administration, inhalation, transdermal application, intradermal application, intravaginal application, topical application, intranasal, or rectal administration. In another embodiment, compositions disclosed herein can be administered intravenously. In another embodiment, compositions can be administered intratumoraly, subcutaneously, intramuscularly, intradermally, or orally.

In some embodiments, HOTAIR-targeting synthetic polynucleotide analog can be administered to a subject in an appropriate pharmaceutical composition including pharmaceutically acceptable carriers, excipients, delivery vehicles, or combinations thereof. In certain embodiments, the delivery vehicle is a liposome formulation. The term "carrier" as used herein is intended to include diluents such as saline and aqueous buffer solutions. Under ordinary conditions of storage and use, these preparations may contain a preservative to prevent the growth of microorganisms.

Although the descriptions of pharmaceutical compositions provided herein are principally directed to pharmaceutical compositions which are suitable for administration to humans, it will be understood by the skilled artisan that such compositions are generally suitable for administration to animals or organisms of all sorts. Modification of pharmaceutical compositions suitable for administration to humans in order to render the compositions suitable for administration to various animals is well understood by the ordinarily skilled veterinary pharmacologist.

In certain embodiments, pharmaceutical compositions suitable for injectable use may be administered by means known in the art. For example, sterile aqueous solutions (where water soluble) or dispersions for the extemporaneous preparation of sterile injectable solutions or dispersion may be used. In all cases, the composition can be sterile and can be fluid to the extent that easy syringability exists. It can further be preserved against the contaminating action of microorganisms such as bacteria and fungi. The pharmaceutically acceptable carrier can be a solvent, stabilizing composition or dispersion medium containing, for example, water, ethanol, polyol (for example, glycerol, propylene glycol, and liquid polyethylene glycol, and the like), and suitable mixtures thereof.

In some embodiments, sterile injectable solutions can be prepared by incorporating the active agent in an appropriate amount with an appropriate solvent or with one or a combination of ingredients enumerated above, as required, followed by sterilization.

In other embodiments, upon formulation, solutions can be administered in a manner compatible with the dosage formulation and in such amount as is therapeutically effective. A therapeutically effective amount is an amount of a biologically active compound that has a single or cumulative beneficial effect on the health or well-being of a patient. The formulations are easily administered in a variety of dosage forms, such as the type of injectable solutions described above. It is contemplated that slow release capsules, timed-release microparticles, and the like can also be employed for administering pharmaceutical compositions herein. These particular aqueous solutions are especially suitable for intravenous, intratumoral, intramuscular, subcutaneous, and intraperitoneal administration.

Methods of Treatment

Certain embodiments provide a method for treating a cancer in a subject using a HOTAIR-targeting synthetic polynucleotide analog. In some embodiments, a cancer can be treated directly by the HOTAIR-targeting synthetic polynucleotide analog. In other embodiments, the HOTAIR-targeting synthetic polynucleotide analog sensitizes cancer cells to another active agent, such as a chemotherapeutic. HOTAIR has been shown to be an oncogenic factor involved in the carcinogenesis and progression of a large number of different cancers. For example, the lncRNA plays a key role in the initiation and progression of both cervical cancer and nasopharyngeal carcinoma, and has been shown to play an important role in promoting malignancy, including proliferation and invasion. HOTAIR has been implicated in many cancers, including but not limited to ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma and pancreatic cancer.

In certain embodiments, HOTAIR-targeting synthetic polynucleotide analogs, pharmaceutical compositions, and methods described herein can be used to treat any disease or condition characterized by overexpression of HOTAIR, including but not limited to ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma, pancreatic cancer, and rheumatoid arthritis. In certain embodiments, the condition to be treated can be ovarian cancer or breast cancer.

In some embodiments, HOTAIR-targeting synthetic polynucleotide analogs can be used to treat breast cancer. In other embodiment, HOTAIR-targeting synthetic polynucleotide analogs can be used to treat ovarian cancer. In some aspects, a chemotherapeutic agent, such as cisplatin, etoposide, or both cisplatin and etoposide, are administered to a subject having ovarian cancer or breast cancer at the same time the HOTAIR-targeting synthetic polynucleotide analog is administered, or sometime thereafter.

HOTAIR expression levels were found to be higher in primary breast tumors than in adjacent noncancerous tissue. qPCR studies showed that HOTAIR expression ranges from over a hundred times greater to nearly two-thousand times greater in breast cancer metastases than those in noncancerous tissue. The overexpression of HOTAIR led to altered histone H3 lysine 27 methylation, gene expression, and increased cancer invasiveness and metastasis in a PRC2-dependent manner, while loss of HOTAIR inhibited cancer invasiveness, particularly in cells possessing excessive PRC2 activity. HOTAIR expression in primary breast tumors has also been shown to be a good predictor of metastasis and mortality.

In ovarian cancer, HOTAIR has been shown to be overexpressed relative to normal ovarian tissue, particularly in poorly differentiated ovarian cancers. Recent studies have identified HOTAIR as an independent prognostic factor for predicting overall survival in serous ovarian cancer patients.

Similar results have been found in other cancers. Studies of pancreatic cancer have shown that HOTAIR expression is higher in cancerous tissue than that in noncancerous pancreatic tissue, and is associated with more aggressive tumors. HOTAIR expression was also found to be significantly higher in hepatocellular carcinoma (HCC) tissue than in adjacent noncancerous tissues. Patients whose HCC tumors overexpressed HOTAIR had increased risk of HCC recurrence following hepatectomy, with overexpression correlating with increased risk of lymph node metastasis. Patients with high HOTAIR expression in the tumor also showed significantly shorter recurrence-free survival.

HOTAIR expression has also been associated with carcinogenesis and metastasis in non-small cell lung. In nasopharyngeal carcinoma, biopsy samples had elevated levels of HOTAIR, which correlated with a poorer prognosis for overall survival rate than those with low HOTAIR expression levels. Overexpression of HOTAIR is also associated with high-grade tumor and metastasis in gastrointestinal stromal tumors, wherein RNAi-mediated knockdown of HOTAIR target genes suppressed tumor cell invasiveness. Similar results to these have been found in other cancers.

In some embodiments, HOTAIR-targeting synthetic polynucleotide analogs described herein can be used to treat rheumatoid arthritis in a subject. In addition to cancers, HOTAIR overexpression has also been identified in blood mononuclear cells and serum exosome of rheumatoid arthritis patients. HOTAIR overexpression was shown to lead to the migration of active macrophage.

Certain embodiments provide methods for treating a subject having a condition characterized by overexpression of HOTAIR. In some embodiments, a method for treating the subject comprise administering to the subject a therapeutically effective amount of a HOTAIR-targeting synthetic polynucleotide analog described herein, or a pharmaceutical composition described herein. The HOTAIR-targeting synthetic polynucleotide analog can be any HOTAIR-targeting synthetic polynucleotide analog capable of hybridizing to HOTAIR and preventing the lncRNA from interacting with PRC2. In a particular embodiment, the HOTAIR-targeting synthetic polynucleotide analog is PNA3, having a nucleotide sequence of 5'-TCTGTAACTC-3' (SEQ ID NO: 14).

In other embodiments, the HOTAIR-targeting synthetic polynucleotide analog is conjugated to a pHLIP, which selectively targets the acidic microenvironment of many tumors. In certain embodiments, the pHLIP has the sequence of SEQ ID NO: 18. In a particular embodiment, the pHLIP of SEQ ID NO: 18 is conjugated to PNA3 (SEQ ID NO: 14).

In embodiments wherein the condition to be treated is a form of cancer, the method can further comprise administering to the subject a therapeutic dose of an appropriate chemotherapeutic agent. In certain embodiments, the chemotherapeutic agent can be a platinum-containing chemotherapeutic, such as cisplatin, carboplatin, and oxaliplatin, nedaplating, triplatin tetranitrate, phenanthriplatin, picoplatin, and satraplatin. In other embodiments, the chemotherapeutic agent can be a topoisomerase inhibitor, such as etoposide, amsacrine, teniposide, and doxorubicin. In some embodiments, the chemotherapeutic agent can be cisplatin or etoposide, or both cisplatin and etoposide.

In certain embodiments, treating cells with a HOTAIR-targeting synthetic polynucleotide analog or pharmaceutical composition described herein can resensitize chemotherapeutic resistant cells to chemotherapy. For example, treating cisplatin-resistant ovarian cancer cells (e.g., cell line A2780_CR5) with PNA3 and cisplatin resulted in an increase in cell apoptosis relative to cells treated with cisplatin and control PNA. Thus, certain embodiments provide for re-sensitizing chemotherapeutic-resistant cells to traditional chemotherapeutics. Cells resistant to traditional chemotherapeutics are contacted with an effective amount of a HOTAIR-targeting synthetic polynucleotide analog or pharmaceutical composition described herein. In certain embodiments, the HOTAIR-targeting synthetic polynucleotide analog is PNA3. Methods for resensitizing a cell to a chemotherapeutic can be carried out in vitro, aiding in the study of chemo-resistant cells, or in vivo, such as in a subject presenting with a chemo-resistant form of a cancer characterized by overexpression of HOTAIR.

In certain embodiments, a subject having a condition characterized by overexpression of HOTAIR can be treated by administering to the subject a pharmaceutically effective amount of a pharmaceutical composition comprising a HOTAIR-targeting synthetic polynucleotide analog described herein. In certain embodiments the HOTAIR-targeting synthetic polynucleotide analog includes a polynucleotide having the nucleic acid sequence, or a part of the nucleic acid sequence of SEQ ID NO: 14. In embodiments where the condition is a cancer, the subject can be administered the pharmaceutical composition prior to administration of a traditional chemotherapeutic agent (e.g., cisplatin and/or etoposide), or concurrently with the administration of the traditional chemotherapeutic agent. The synthetic polynucleotide analog and traditional chemotherapeutic agent can be administered together in the same pharmaceutical composition, or can be administered separately in two distinct pharmaceutical compositions. In certain embodiments, the pharmaceutical composition is administered directly to a solid tumor (i.e., intratumoraly). In other embodiments, the pharmaceutical composition is administered intravenously or orally.

In certain embodiments, the pharmaceutical composition can be administered to the subject in a single dose, or in multiple doses. Where the pharmaceutical composition comprising the HOTAIR-targeting synthetic polynucleotide analog is administered to the subject concurrently with a traditional chemotherapeutic agent, the pharmaceutical composition comprising the HOTAIR-targeting synthetic polynucleotide analog can be administered to the subject according to current treatment protocols for the cancer to be treated. In some embodiments, the pharmaceutical composition can be administered between treatments with a traditional chemotherapeutic. The pharmaceutical composition can be administered, for example, daily, every two days, every three days, every four days, every five days, every six days, weekly, bi-weekly, or monthly, whether in connection with administration with a traditional chemotherapeutic agent or not. In certain embodiments, the pharmaceutical composition can be administered daily for a period of 1 to 7 days prior to a scheduled treatment with a traditional chemotherapeutic. Such a treatment regimen allows for the resensitization of the tumor to the traditional chemotherapeutic agent, as discussed above.

Determining HOTAIR Expression

Certain embodiments provide for determining HOTAIR expression in a sample. HOTAIR expression in a test sample can be determined utilizing HOTAIR-targeting synthetic polynucleotide analogs described herein tagged with a fluorescent molecule or fluorophores. The sample to be tested can be a cell line, or cells isolated from a biopsy or other biological sample from a subject. Fluorescent-tagged HOTAIR-targeting synthetic polynucleotide analogs are contacted and incubated with the test sample prior to analysis. The fluorescent signal in the test sample is then determined, thereby indicating HOTAIR expression. Fluorescent molecules that can be tagged to a HOTAIR-targeting synthetic polynucleotide analog described herein include, but are not limited to fluorescein, green fluorescent protein, rhodamine, cyanine dyes, and Alexa dyes.

In certain embodiments, the test sample can be a cell line or cells isolated from a biopsy or other biological sample known or suspected of overexpressing HOTAIR. Thus, the test sample may be derived from a subject having or suspected of having a disease or condition characterized by HOTAIR overexpression.

Resulting fluorescence can be determined by any method known in the art. In certain embodiments, fluorescence is determined by fluorescence microscopy. Quantitative fluorescence microscopy can be used to determine HOTAIR expression in a test sample relative to a control sample comprising cells known to have normal HOTAIR expression.

In some embodiment, in addition to determining HOTAIR expression, fluorescent-tagged PNAs described herein can also be used to observe and determine subcellular localization of HOTAIR.

Diagnosis and Determination of Risk

As described above, HOTAIR expression is elevated in many types of cancers. It therefore stands that HOTAIR can serve as a diagnostic biomarker. In certain embodiments, a HOTAIR-targeting synthetic polynucleotide analog can be used in a method for diagnosing a subject as having a condition characterized by overexpression of HOTAIR. In other embodiments a HOTAIR-targeting synthetic polynucleotide analog can be used in a method for determining the risk of a subject for developing a condition characterized by overexpression of HOTAIR.

In certain embodiments, HOTAIR expression can be determined in both a test sample and in a control sample, as described above. Fluorescent signal levels determined for the test sample are compared to fluorescent signal levels determined for the control sample. In an embodiment, the comparison is made with the results of quantitative fluorescence microscopy obtained from both samples. The subject from which the test sample was obtained is diagnosed as having or identified as being at risk of having a condition characterized by overexpression of HOTAIR when the fluorescent signal levels in the test sample are higher than the fluorescent signal levels in the control sample.

In a particular embodiment, the diagnosis or identification of risk can be made when the fluorescent signal levels in the test sample are at least about 125-fold greater than in the control sample. In other embodiments, the diagnosis or identification of risk can made when the fluorescent signal levels in the test sample are at least about 800-fold greater than in the control sample. In yet other embodiments, the diagnosis or identification of risk is made when the fluorescent signal levels in the test sample are at least about 1,000-fold greater than in the control sample. These diagnosis values are consistent with the overexpression of HOTAIR observed in at least breast cancer.

In some embodiments, if a condition characterized by overexpression of HOTAIR is diagnosed, or a risk of such a condition is identified, additional diagnostic tests can be ordered or performed. Additional diagnostic tests for the conditions identified herein as being characterized by overexpression of HOTAIR are known in the art, and those skilled in the art will be able to readily identify which additional diagnostic tests can be performed for any given condition. In certain embodiments, the diagnostic methods described herein are conducted in parallel with one or more traditional diagnostic tests. As such, the diagnostic methods described herein can serve as either a preliminary diagnostic, or a supplemental diagnostic.

Immunoprecipitation

In certain embodiments, HOTAIR-targeting synthetic polynucleotide analogs can also be used in immunoprecipitation assays useful in binding and identifying HOTAIR binding partners. Biotin or other cofactors can be conjugated to either the 5' or 3' end of the synthetic polynucleotide analog. Immunoprecipitating lncRNAs is a notoriously difficult and technically challenging technique due to the unspecific binding of currently used oligos. By using HOTAIR-targeting synthetic polynucleotide analogs, the specificity of binding is greatly improved. In a particular embodiment, the target specific HOTAIR-targeting synthetic polynucleotide has the nucleotide sequence of 5-TCTGTAACTC-3' (SEQ ID NO: 14), or a nucleotide sequence that is complementary to the nucleotide sequence of 5'-TCTGTAACTC-3' (SEQ ID NO: 14).

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to adapt it to various usages and conditions.

Example 1. Inhibiting HOTAIR and EZH2 Alters Platinum Sensitivity and Cancer Cell Function In one exemplary method, the effect of inhibiting both HOTAIR and EZH2 on cancer cell survival was investigated. A highly platinum-resistant ovarian cancer cell line (A2780_CR5) was treated with dsiRNA targeting HOTAIR and/or a pharmacological inhibitor of EZH2 (GSK126), followed by survival assays. As an additive ($P<0.05$) effect of inhibiting HOTAIR-EZH2 on drug sensitivity and survival was observed (versus inhibiting either factor alone; FIG. 2A), it was next of interest to target the HOTAIR-EZH2 interaction by targeting the 89-mer minimum interacting region of HOTAIR, which has been shown. mFold (Zuker, M., *Mfold web server for nucleic acid folding and hybridization prediction*. Nucleic acids research, 2003. 31(13): 3406-3415, incorporated herein by reference in its entirety) was used to validate the predicted secondary structure of this site, observing a highly predicted, single-stranded region in all 19 predicted structures, which complemented previous such structures (FIG. 3A).

Figure 4A:
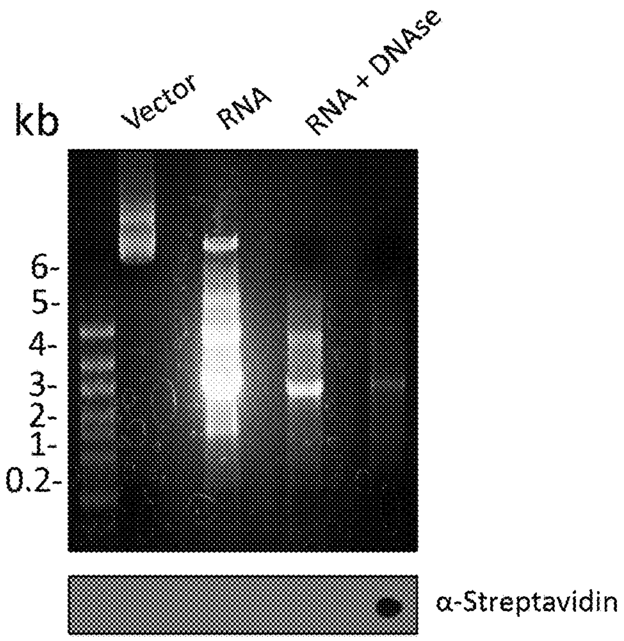
FIG. 4A shows the in vitro transcription and biotinylation of full-length HOTAIR RNA.

In one exemplary method, nucleic acids (PNAs) complementary to the single stranded region of the 89-mer domain were then designed (FIG. 3B). The individual PNAs (PNAs 1-5, Table 1) were combined with in vitro transcribed, biotinylated full-length HOTAIR (1 μM) and recombinant EZH2 (FIG. 4A). Of the five PNAs examined (1 μM each), only PNA3 reduced (approximately 80%) the HOTAIR-EZH2 interaction (FIG. 2B), with essentially no effect observed for the other PNAs and importantly, none of the PNAs altered the EZH2-ALU (control RNA) interaction (FIG. 2B), further demonstrating specificity of PNA3 for inhibiting the HOTAIR-EZH2 interaction.

Figure 2C:
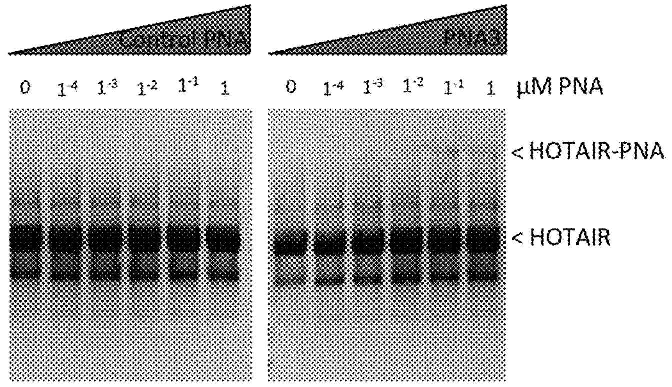
FIG. 2C shows binding of pNA3 or control PNA in vitro to transcribed HOTAIR.
Figure 2D:
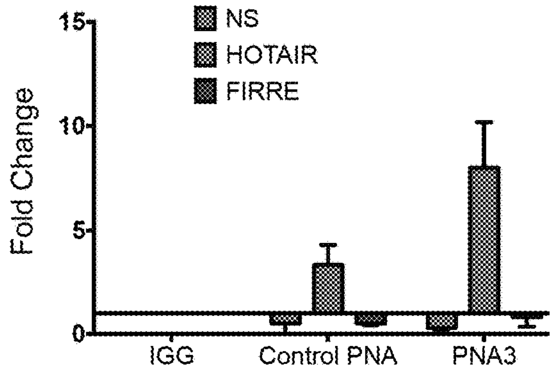
FIG. 2D is a bar graph showing an 8-fold enrichment of HOTAIR with PNA3 compared to control PNA.

In another exemplary method, binding of PNA3 or control PNA to in vitro transcribed HOTAIR was examined using gel shift assay. At 1×1-2 μM PNA3, a shifter band was observed (FIG. 2C), whereas no observable band shift was seen with control PNA. The ability of PNA3 to bind HOTAIR from HEK293 cell lysate ectopically overexpressing full length HOTAIR was also examined. An 8-fold enrichment of HOTAIR with PNA3 compared to control PNA was detected by qRT-PCR (FIG. 2D), whereas no such enrichment was observed using non-specific primer control and primers corresponding to the lncRNA FIRRE (FIG. 2D), demonstrating specific PNA3-HOTAIR binding in vivo.

Figure 4C:
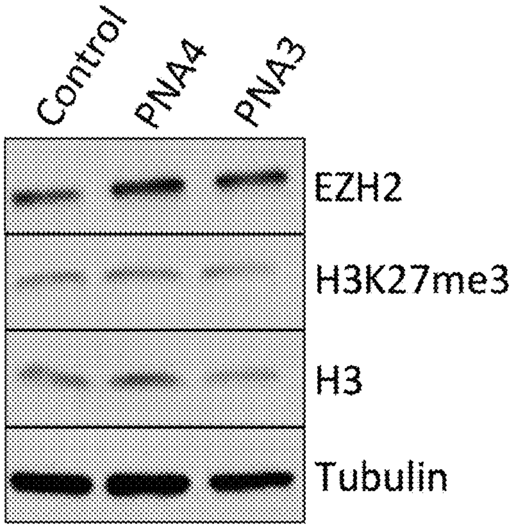
FIG. 4C shows total H3k27me3, H3, EZH2 and β-tubulin levels after treatment of in A2780_CR5 cells for 48 hrs with water (control), control PNA (1 μM) or PNA3 (1 μM).
Figure 4B:
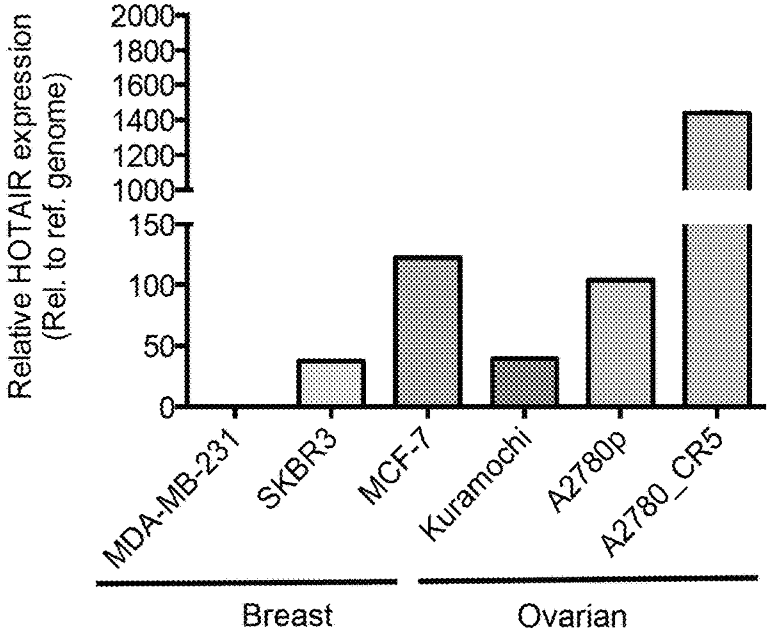
FIG. 4B shows the relative HOTAIR expression in breast (SKBR-3, MCF, and MDA-MB-231) and ovarian (A2780p, A2780_CR5, and Kuramochi) cancer cell lines.
Figure 5A:
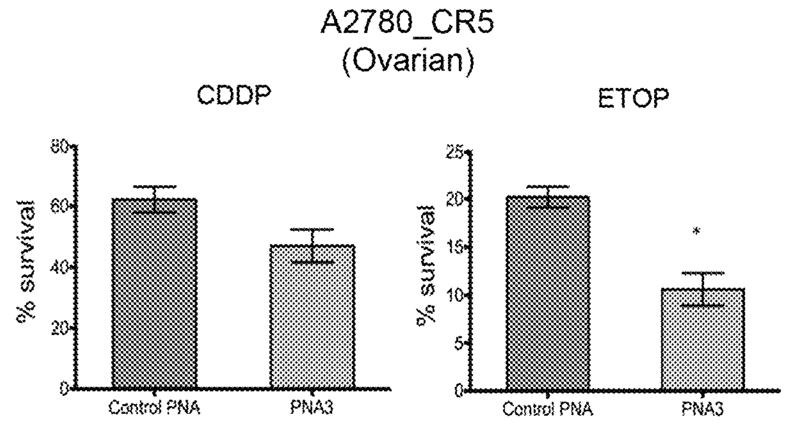
FIGS. 5A-5C are bar graphs showing percent survival (A) or caspase 3/7 cleavage (indicates apoptosis) (B-C) in the noted cells following treatment with control PNA or PNA3 with either cisplatin (CDDP) or etoposide (ETOP). Asterisks indicate P<0.05 (*) or P<0.01 (**).
Figure 6A:
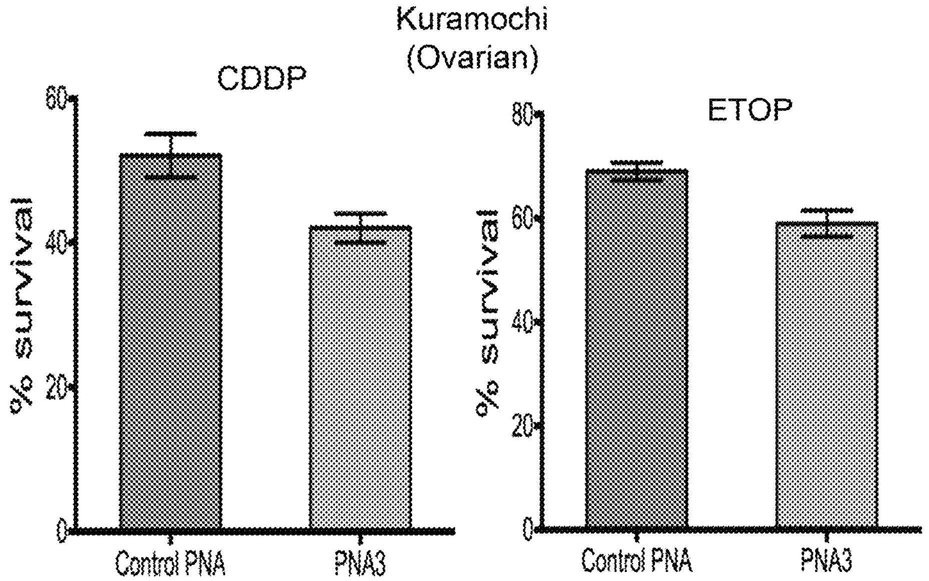
FIGS. 6A-6D are bar graphs showing the percent survival of the noted cells following treatment with PNA3 and either cisplatin (CDDP) or etoposide (ETOP). Asterisks indicate P<0.05 (*) or P<0.01 (**).
Figure 6B:
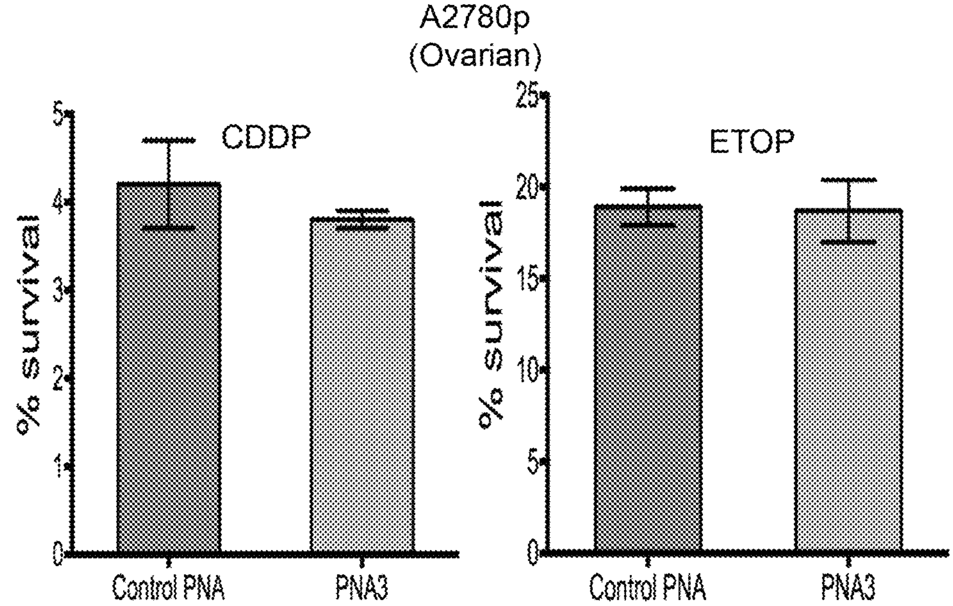
Figure 6C:
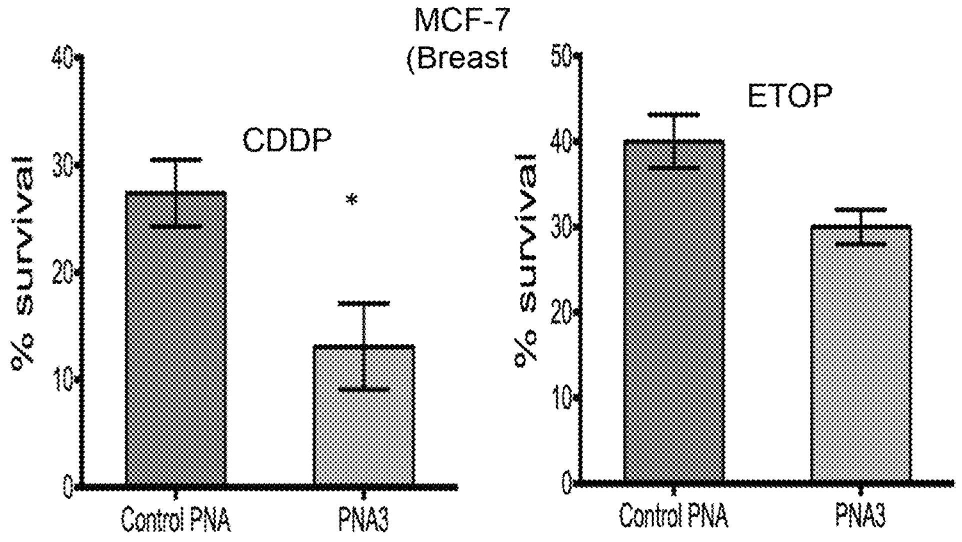
Figure 6D:
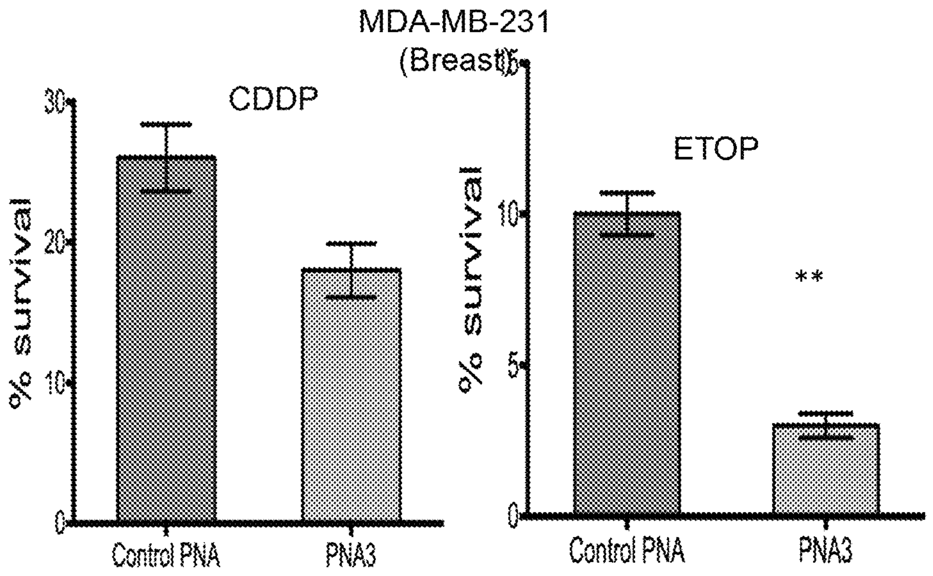

In one exemplary method, the effect of PNA3 on HOTAIR-expressing ovarian (A2780p, A2780_CR5 and Kuramochi) and breast (MCF-7, SKBR-3, and MDA-MB-231) cancer cells (FIG. 4B, Table 2) was examined. Cells were treated with PNA3 or control PNA (1 μM each; alone or in combination with chemotherapeutics cisplatin (CDDP) or etoposide). Functional assays (clonogenic survival, caspase 3/7 cleavage, and proliferation assays) were performed, and EZH2 and histone H3 lysine K27 trimethylation (H3K27me3) levels were examined. PNA3-CDDP or -etoposide treatment inhibited (P<0.05) clonogenic survival of CDDP-resistant A2780_CR5 (0.8-fold or 0.5-fold respectively, compared to control PNA-chemotherapy combinations; FIG. 5A) and to a lesser extent Kuramochi (0.9-fold CDDP, 0.9-fold etoposide), and breast cancer cell lines MCF-7 (0.4-fold CDDP, 0.8-fold etoposide) and MDA-MB-231 (0.7-fold CDDP, 0.3-fold etoposide) (FIGS. 6B-6D). These combinations had no effect on survival of CDDP-sensitive A2780p cells (FIG. 6B). SKBR-3 breast cancer cells do not form colonies and clonogenic survival data for these cells could not be obtained.

TABLE 1

PNA sequences.

| Sense (5'-3') | Sequence | SEQ ID NO(s) |
|---|---|---|
| PNAs with cell penetrating peptide | | |
| PNA1 | RRRQRRKKR-TACTGCAGGC | 19 linked to 12 |
| PNA2 | RRRQRRKKR-GTAACTCTGGG | 19 linked to 13 |
| PNA3 | RRRQRRKKR-TCTGTAACTC | 19 linked to 14 |
| PNA4 | RRRQRRKKR-CTCCCCTACTGC | 19 linked to 15 |
| PNA5 | RRRQRRKKR-CCCTCTCTCC | 19 linked to 16 |
| Control PNA | RRRQRRKKR-CTCCCTTCAA | 19 linked to 17 |
| Sense (5'-3') | | |
| Thiolated Cy3 labeled PNAs | | |
| PNA3 | ooo-TCTGTAACTC-ooo-Cys-Cy3 | 14 (thiolated) |
| PNA4 (Control) | ooo-CTCCCCTACTGC-ooo-Cys-Cy3 | 15 (thiolated) |
| Sense (5'-3') | | |
| Thiolated PNAs used in in vivo mouse study | | |
| PNA3 | ooo-TCTGTAACTC-ooo-Cys | 14 (thiolated) |
| PNA4 (Control) | ooo-CTCCCCTACTGC-ooo-Cys | 15 (thiolated) |

TABLE 2

Cell lines used.

| Cell type | Cancer Type | Putative histology | TP53 Mutational profile |
|---|---|---|---|
| A2780p | ovarian | Endometroid | Wild-type |
| A2780_CR5 | ovarian | Endometroid | Wild-type |
| KURAMOCHI | ovarian | High Grade Serous | Mutant p.D281Y(Hm) |

TABLE 2-continued

Cell lines used.

| Cell type | Cancer Type | Putative histology | TP53 Mutational profile |
|---|---|---|---|
| SKBR-3 | breast | adenocarcinoma/ER (−) HER2(+) | Mutant p.R175H |
| MCF-7 | breast | ER(+), HER2(+), PR(+) | Wild-type |
| MDA-MB-231 | breast | epithelial adenocarcinoma/ ER(−), HER2(−), PR(−) | mutant |

Tp53 mutations are shown as heterozygous (het) or homozygous (Hm) at indicated residues.

Figure 5B:
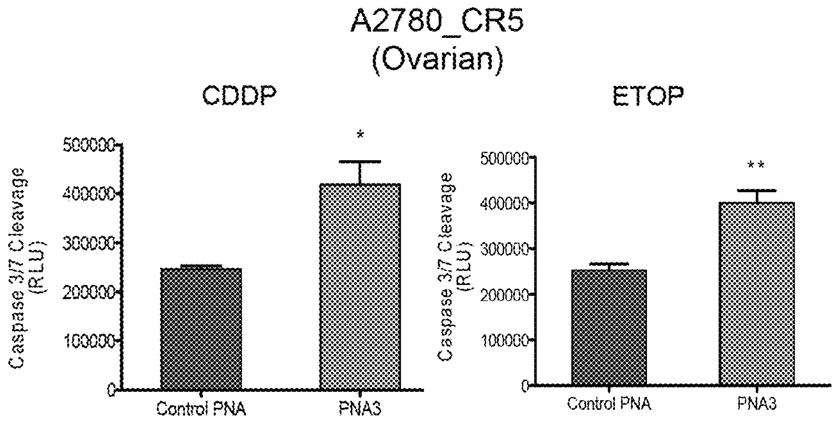
Figure 5C:
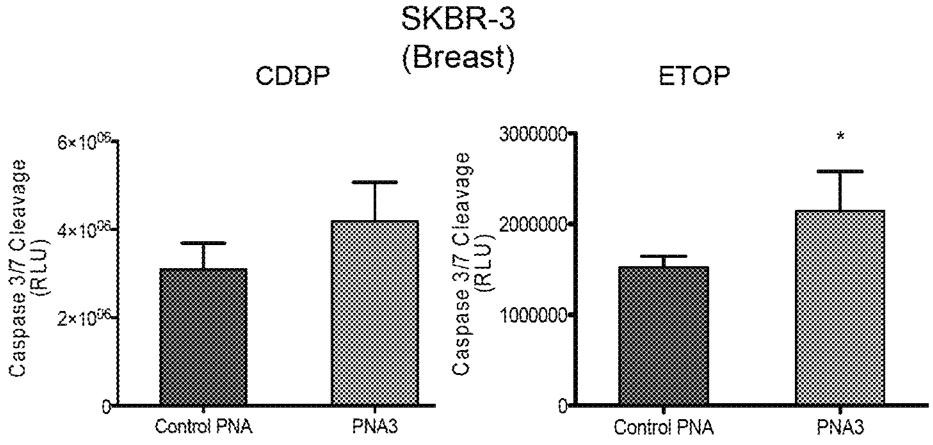
Figure 7A:
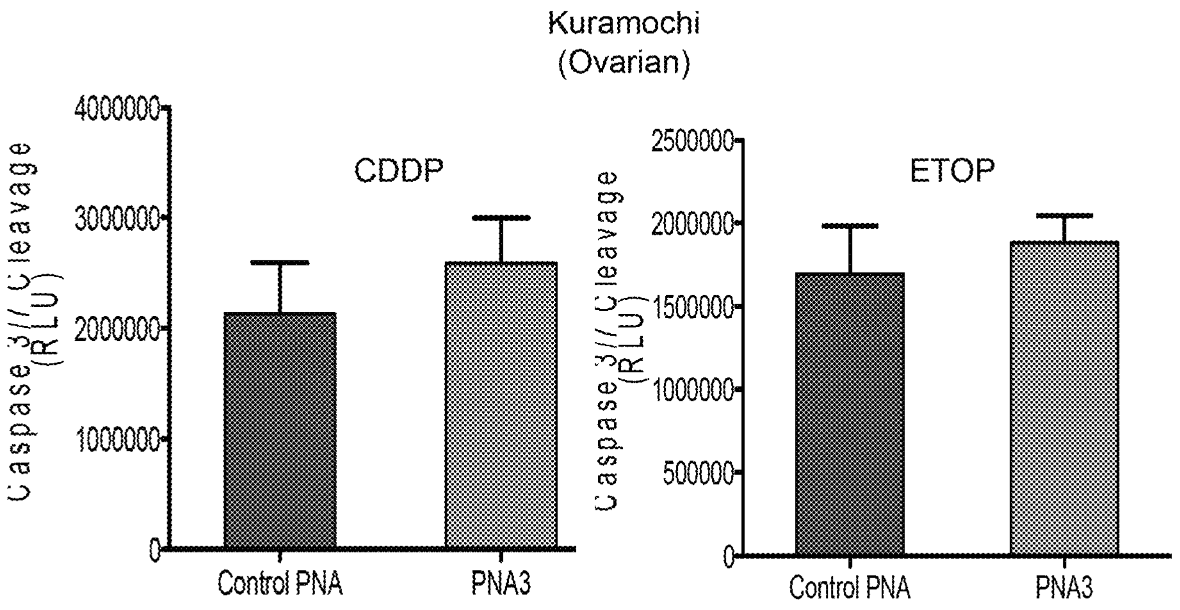
FIGS. 7A-7D are bar graphs showing the caspase 3/7 cleavage (indicates apoptosis) in cells following treatment with PNA3 and either cisplatin (CDDP) or etoposide (ETOP). Asterisks indicate P<0.05 (*) or P<0.01 (**).
Figure 7B:
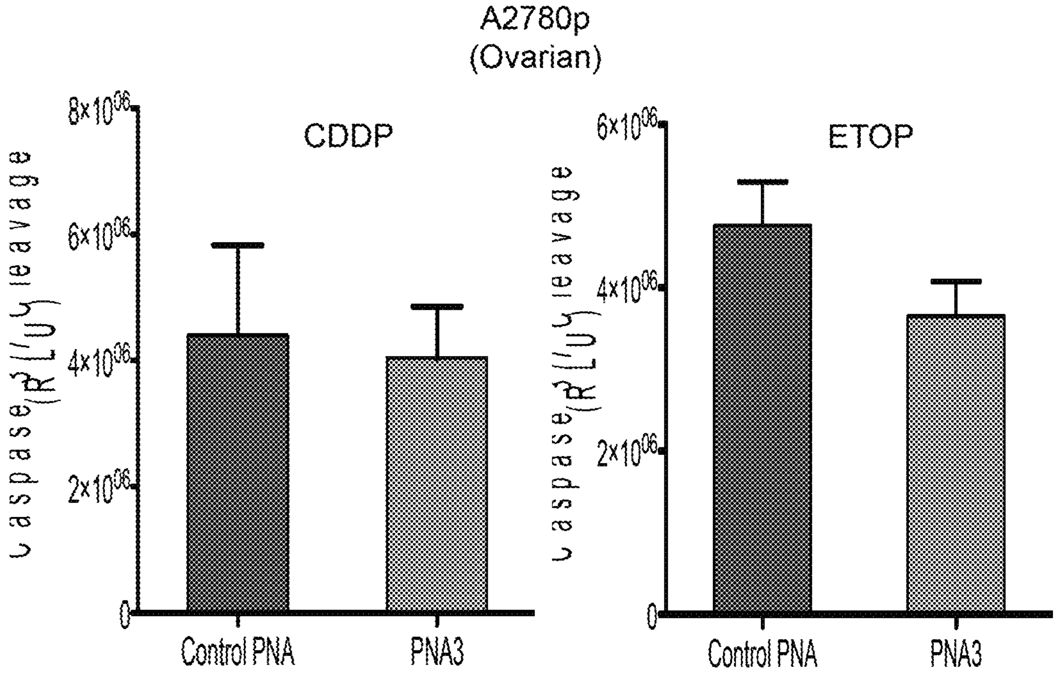

Consistent with the clonogenic data, increased (P<0.05) caspase 3/7 cleavage was observed for ovarian (A2780_CR5: 1.7-fold CDDP and 1.8-fold etoposide, FIG. 5B; Kuramochi: 1.2-fold change CDDP and 1.2-fold etoposide, FIG. 7A) and breast (SKBR-3: 1.3-fold CDDP and 1.3-fold etoposide, FIG. 4C; MCF-7: 1.3-fold CDDP and 1.2-fold etoposide, FIG. 7C; MDA-MB-231: 1.5-fold CDDP and 1.2-fold etoposide, FIG. 7D) cancer cell lines, with no effect on A2780p cells (FIG. 7B). In addition, no effect of PNA3 on ovarian or breast cancer cell proliferation was observed (FIGS. 8A-8F).

Figure 5D:
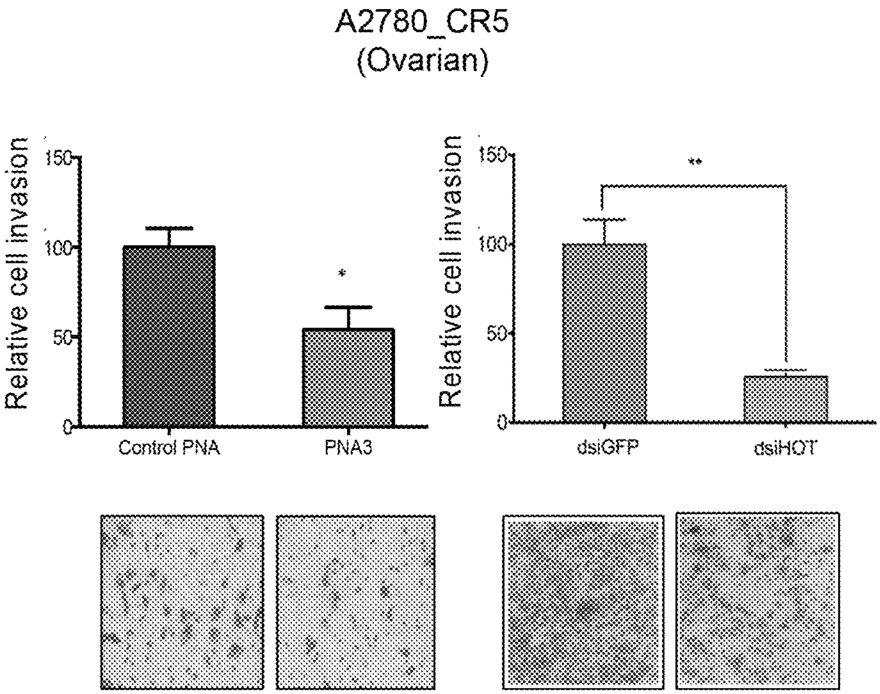
FIGS. 5D-5E show bar graphs and light microscope images, which both show a decrease in cell invasion following administration of PNA3 or dsiHOTAIR. Asterisks indicate P<0.05 (*) or P<0.01 (**).
Figure 5E:
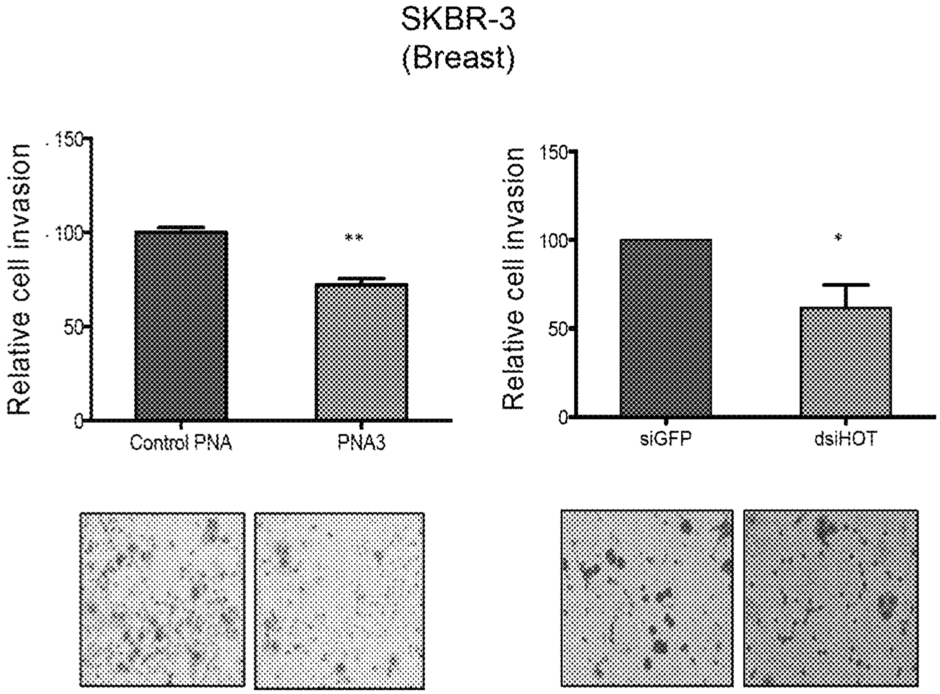
Figure 9A:
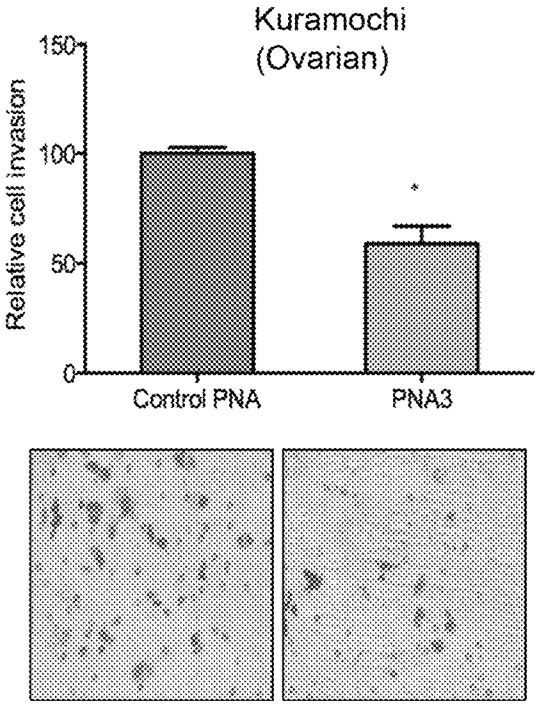
FIGS. 9A-9C are bar graphs showing bar graphs and light microscope image showing invasion assay results. Asterisks indicate P<0.05 (*) or P<0.01 (**).
Figure 9B:
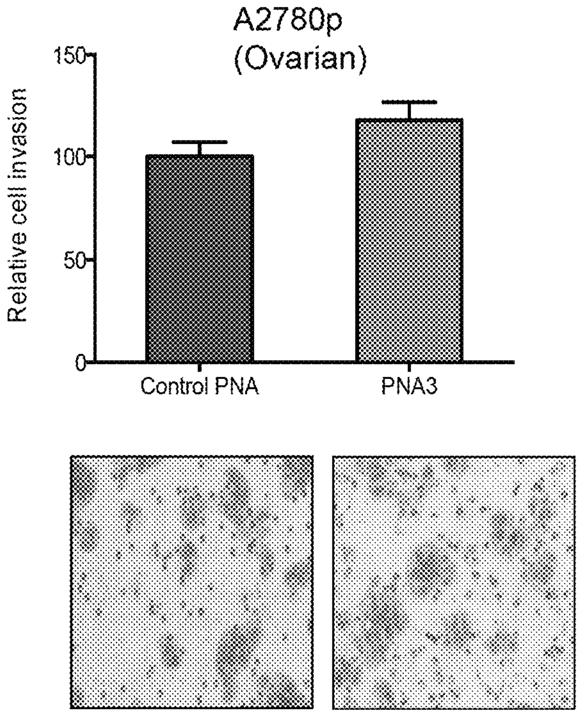
Figure 9C:
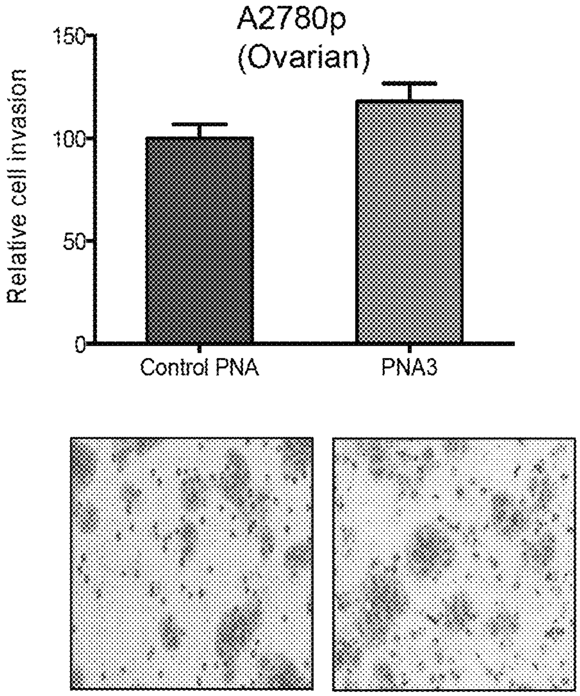

In another exemplary method, ovarian cancer cells and breast cancer cells were treated with PNA3 or control PNA. Decreased (P<0.05) invasion of A2780_CR5 (2-fold, FIG. 5D), Kuramochi (0.6-fold, FIG. 9A) and SKBR-3 (2-fold, FIG. 5E) was observed, and the effect of PNA3 on cell invasion was essentially similar to knocking-down HOTAIR expression using siRNA (FIGS. 5D-5E). PNA3 or control PNA had no effect on A2780p and MDA-MB-231 cell invasion (FIGS. 9B-9C).

Figure 7C:
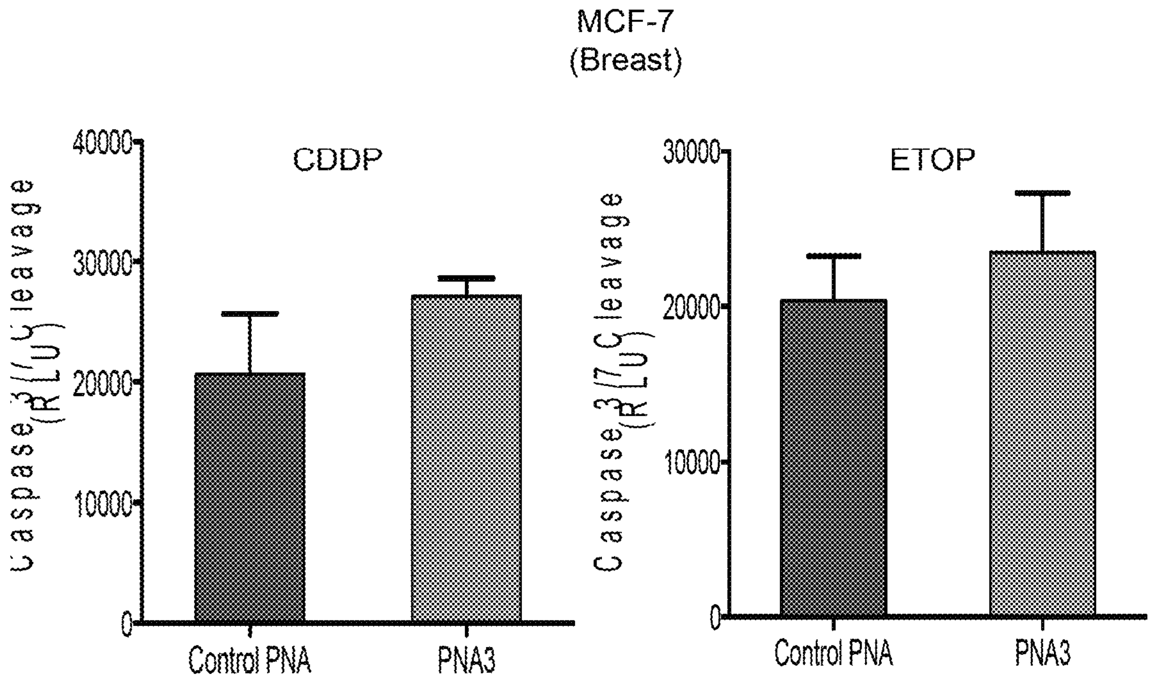
Figure 7D:
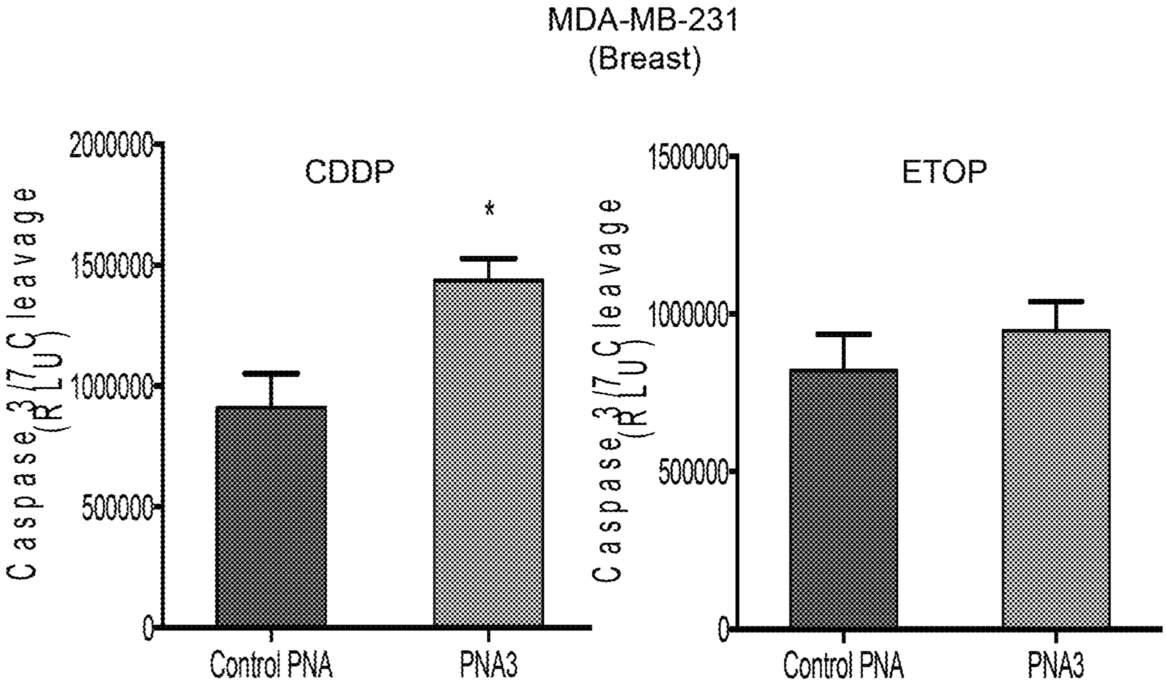
Figure 8A:
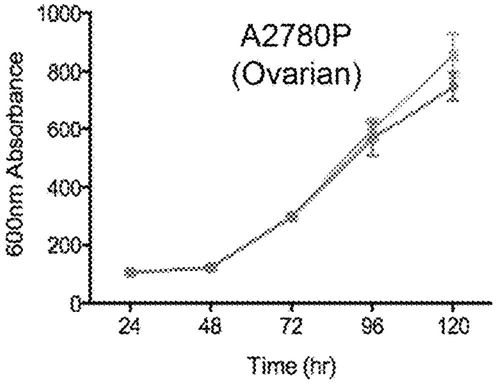
FIGS. 8A-8F are line graphs showing the proliferation assay results.
Figure 8D:
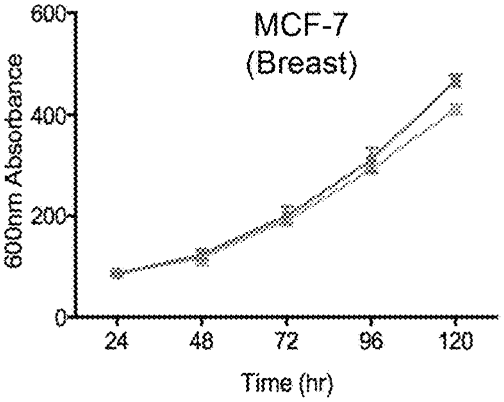
Figure 8B:
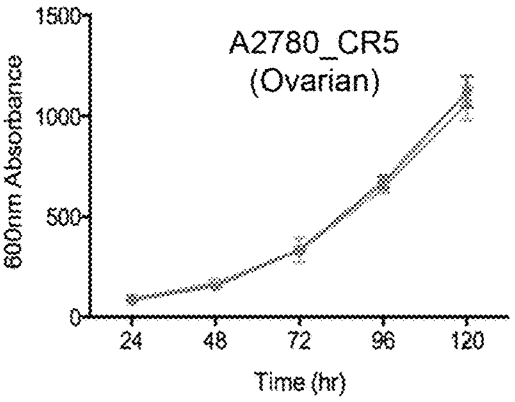
Figure 8E:
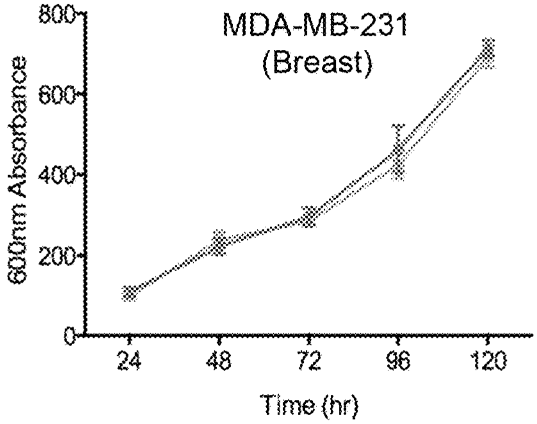
Figure 8C:
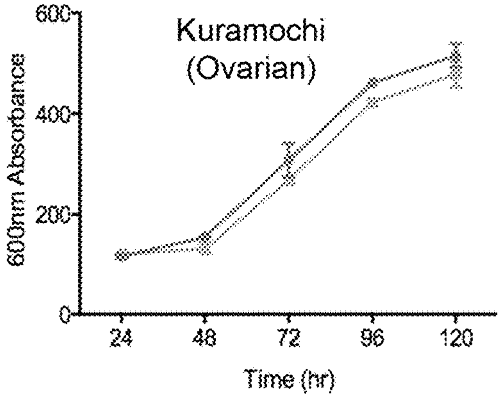
Figure 8F:
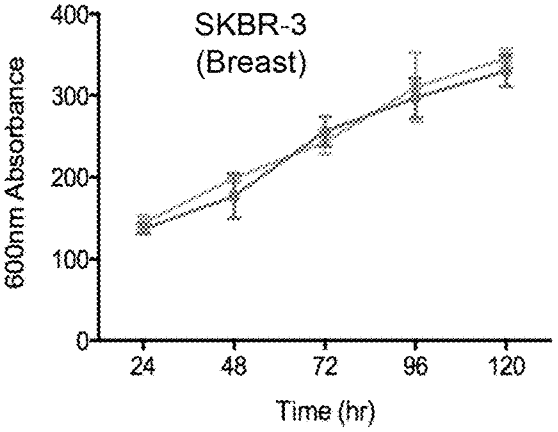
Figure 10A:
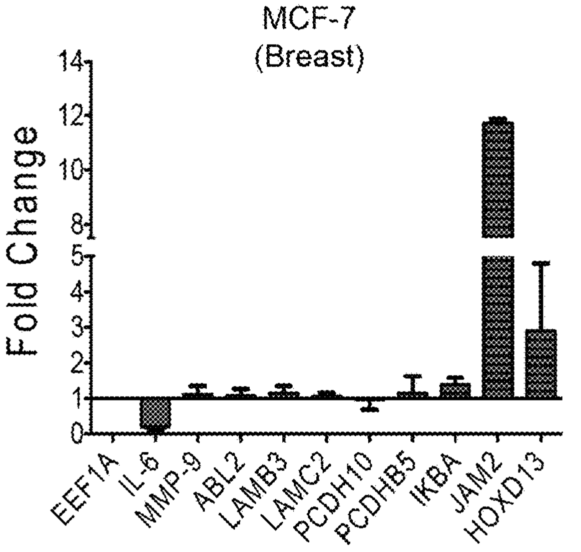
FIGS. 10A-10D are bar graphs showing HOTAIR target gene expression in the noted cell lines following treatment with either PNA3 or control PNA.
Figure 10B:
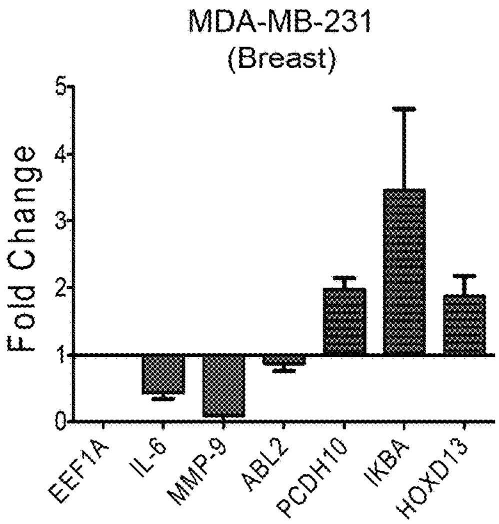
Figure 10C:
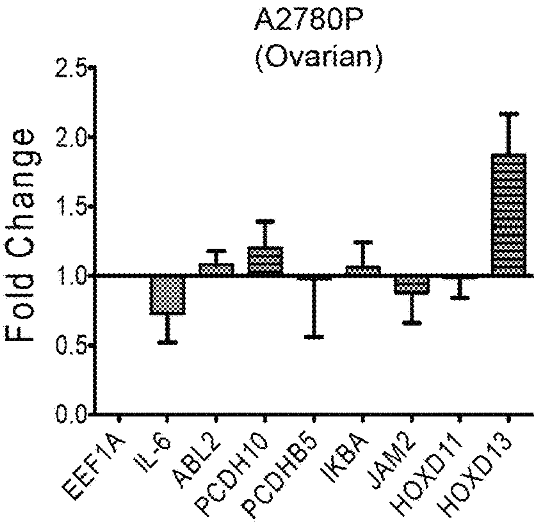
Figure 10D:
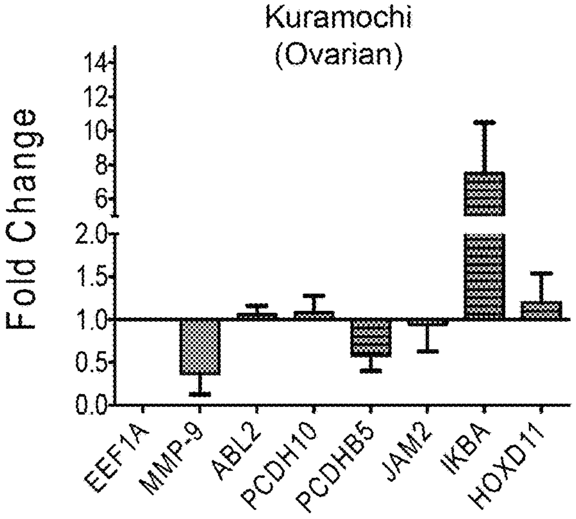

Example 2. Effect of pHLIP-Conjugated PNA3 on CDDP Sensitivity, Tumor Formation, and Survival In another exemplary method, gene expression levels were measured for those genes previously shown to be up- (IL6, MMP9, ABL2, LAMB3, LAMC2) or down- (IKBα, JAM2, HOXD11, HOXD13, PCDH10, and PCDHBS) regulated by HOTAIR using qRT-PCR (48 hrs post-PNA treatment) to investigate the effect of PNA3 or control PNA on HOTAIR target gene expression. When compared to control PNA consistent decreased expression of IL-6 and MMP-9 and increased JAM2, HOXD13 and IKBA expression was observed in the majority of ovarian (A2780_CR5, FIG. 5F; A2780p and Kuramochi, FIGS. 10C-10D) and breast (SKBR-3, FIG. 5G; MCF-7 and MDA-MB-231, FIGS. 10A-10B) cancer cell lines examined (some genes omitted from graphs due to very high threshold cycle (CT) values or no detection of expression in some of the cell lines examined). Although PNA3 treatment altered HOTAIR target gene expression, the PNA had no effect on total EZH2 and H3K27me3 levels (FIG. 7C).

Figure 11A:
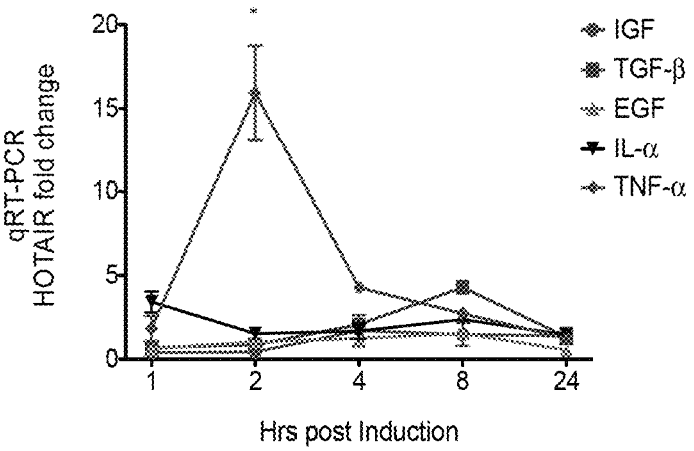
FIG. 11A is a line graph showing changes in HOTAIR target gene expression in A2780 p cells treated with IGF, TGF-β, EGF, IL-1α, or TNF-α (10 ng/mL). Asterisks indicate P<0.05 (*) or P<0.01 (**).
Figure 11B:
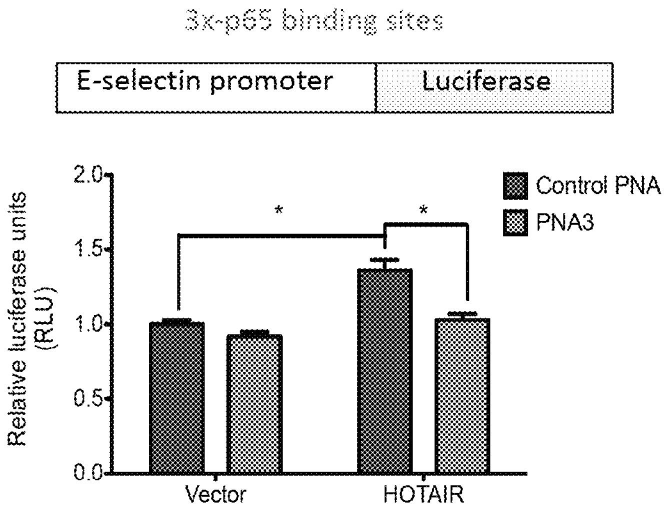
FIG. 11B shows the luciferase activity of A2780p cells transfected with E-Selectin promoter carrying 3× p65-NF-1d3 binding sites and either ectopically overexpressing HOTAIR or vector control treated with or without PNA3 or control PNA. Asterisks indicate P<0.05 (*) or P<0.01 (**).
Figure 11C:
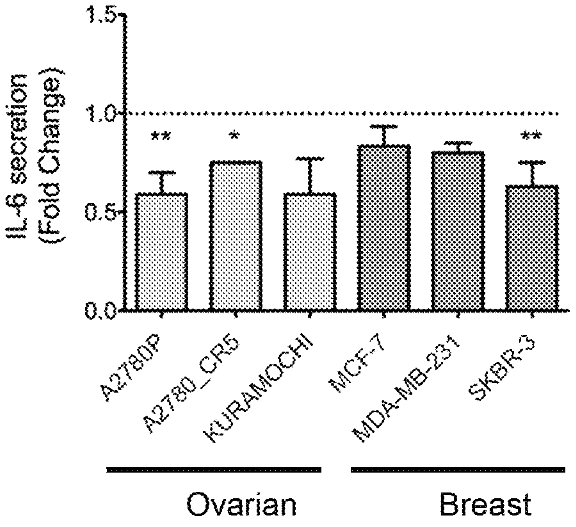
FIG. 11C shows IL-6 secretion by the noted cell lines 48 hrs after treatment with either PNA3 or control PNA. Asterisks indicate P<0.05 (*) or P<0.01 (**).
Figure 11D:
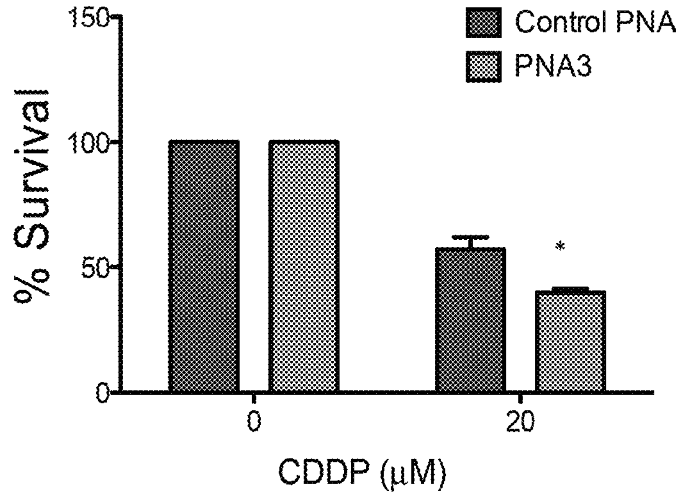
FIG. 11D shows percent survival of A2780P cells treated with CDDP (20 μM using conditioned media from PNA3 or control PNA. Asterisks indicate P<0.05 (*) or P<0.01 (**).

As a positive association between HOTAIR and the master transcription factor NF-κB has been reported. The inventors recently demonstrated that NF-κB-mediated transcriptional regulation of HOTAIR produced epigenetic silencing of Iκ-Bα by HOTAIR, resulting in a positive feedback loop that ultimately increased NF-κB activation. In an exemplary method, a cytokine/chemokine screen was performed, followed by the measurement of HOTAIR levels. Of the cytokines examined, HOTAIR expression was increased (P<0.05) by TNF-α (>15-fold) and TGF-β (5-fold) compared to control (FIG. 11A). To further confirm HOTAIR induction of NF-κB, a luciferase reporter construct containing the E-selectin promoter was used (861 base pairs containing 3 canonical NF-κB-p65-binding sites as a positive control; FIG. 3B) (Ozes, O. N., et al., *NF-κB activation by tumour necrosis factor requires the Akt serine-threonine kinase*. Nature, 1999. 401(6748):82-85, incorporated herein by reference in its entirety) and a 1.4-fold increase (p<0.05) in luciferase activity was observed by ectopic overexpression of HOTAIR compared to vector control (FIG. 11B), which was decreased (P<0.05) by PNA3 (FIG. 11B). PNA3 treatment of breast and ovarian cancer cells decreased (P<0.05) IL-6 secretion into the media (FIG. 11C). Because secreted IL-6 contributes to chemoresistance and induction of cancer stem cells by inducing Aldehyde Dehydrogenase (ALDH1A1), a survival assay was performed with conditioned media (CM) from ovarian cancer cells treated for 24 hours with either PNA3 or control PNA. Increased (P<0.05) sensitivity to CDDP was observed in cells treated with PNA3 CM vs. control CM (FIG. 11D), showing that inhibiting IL-6 secretion altered chemosensitivity.

Figure 11E:
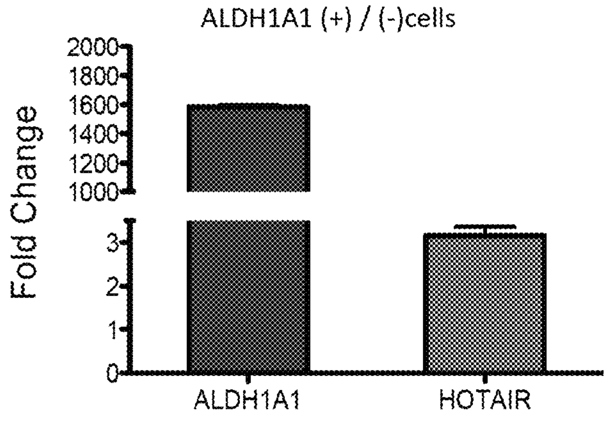
FIG. 11E shows ALDH1A and HOTAIR expression in A2790 CR5 cells.
Figure 11F:
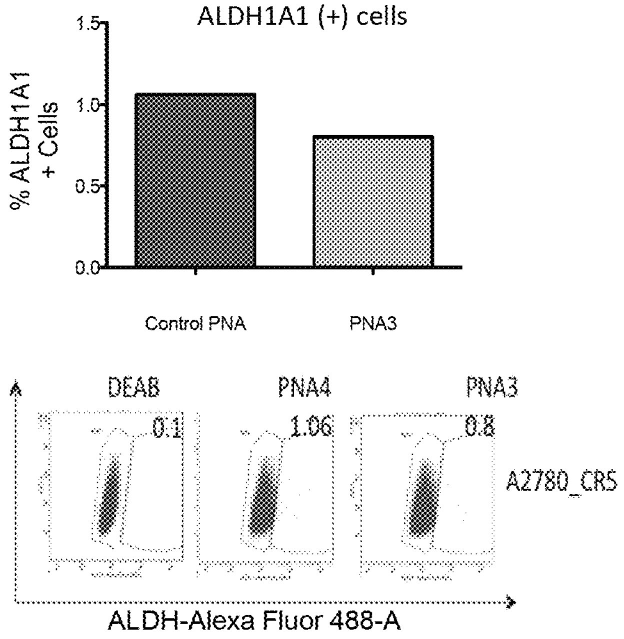
FIG. 11F shows ALDH1A1 activity in A2780 CR5 cells treated with PNA3 or control PNA, as determined by flow cytometry.

In another exemplary method, HOTAIR levels in ALDH1A1 positive A2780_CR5 cells vs. negative were measured. A roughly 1600-fold increase in ALDH1A1 expression (positive control) as well as a 3-fold increase in HOTAIR expression was observed, agreeing with the IL-6 secretion (FIG. 11E). A2780_CR5 cells were then treated with either PNA3 (1 μM) or Control PNA (1 μM). A 25% decrease in ALDH1A1 activity was observed (FIG. 11F), showing that HOTAIR inhibition with PNA can reduce cancer stem cell population, a driver of tumorigenesis and chemotherapy resistance.

Example 3. Effect of pHLIP-Conjugated PNA3 on CDDP Sensitivity, Tumor Formation, and Survival An acidic tumor micro-environment (pH~6 vs pH 7), due to increased glycolysis resulting in lactic acidosis (Warburg effect), has been widely reported for solid tumors including breast and ovarian cancers. In an exemplary method, to target PNAs to the acidic tumor microenvironment, pH-low insertion peptides (pHLIPs) were used, which are unstructured peptides in either neutral pH or basic pH, and can thus interact with the outer surface of lipids in a reversible manner (FIG. 12A). Thiolated pHLIP peptide was conjugated to PNA3 and control PNA (verified using tricine SDS-PAGE gel, FIG. 12B) and under normal pH and acidic pH conditions, pHLIP-PNA cell entry was examined using immunofluorescence. Signals in cytoplasm, nucleus and cell periphery (likely endocytosis) were observed (FIG. 12C).

In another exemplary method, to validate that PNA3 could resensitize A2780_CR5 cells to CDDP, cells were treated with either pHLIP-conjugated PNA3 (1 μM) or control PNA (1 μM) under normal (pH 7.2) or acidic (pH 6.0) conditions and various CDDP concentrations (15-45 μM). An MTT survival assay was performed. No change in cell survival was observed between pHLIP-PNA3 and pHLIP-control under normal pH, however in pH 6, pHLIP-PNA3 decreased (p<0.05) survival (FIG. 12D), indicating successful HOTAIR targeting and altered CDDP-sensitivity under acidic conditions.

Figure 14A:
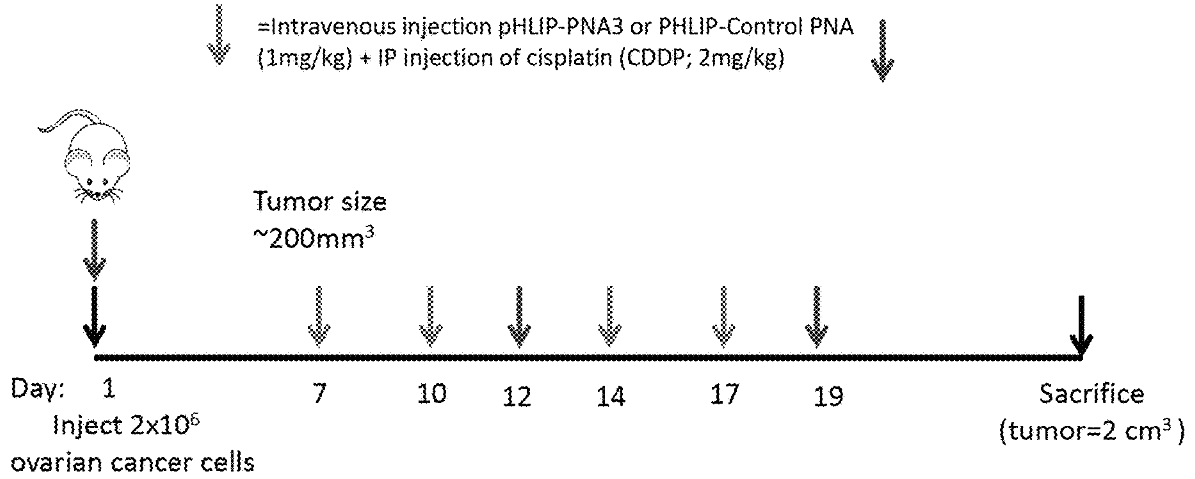
FIG. 14A is a schematic of the mouse treatment schedule.
Figure 14B:
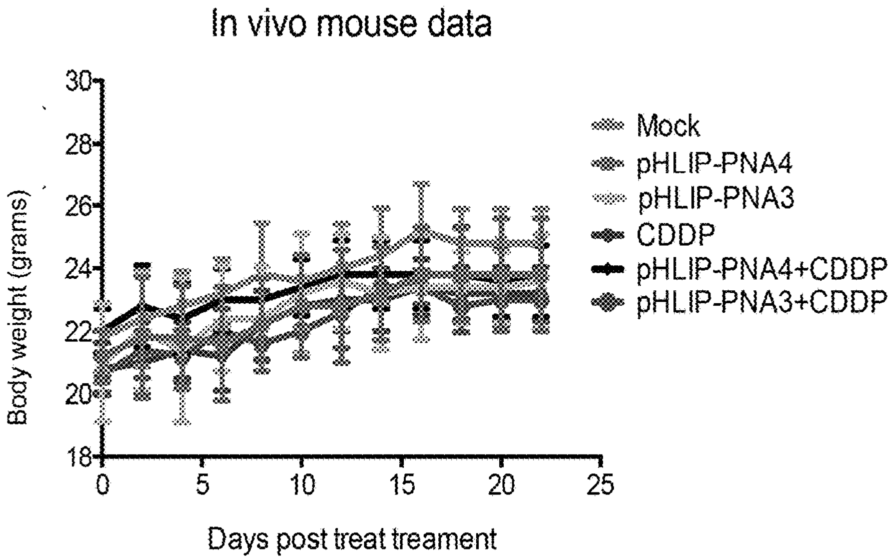
FIG. 14B is a line graph showing the effect of the noted treatments on body weight.

In another exemplary method, to investigate anti-tumor properties of pHLIP-PNA3 in vivo, BALB/C mice were subcutaneously injected with CDDP-resistant A2780_CR5 (2×106 cells). Once tumors reached ~200 $mm^3$, mice were injected intravenously (two times per week for 2 weeks) with pHLIP-PNA3 (1 mg/kg), pHLIP-control PNA (1 mg/kg), and/or CDDP (2 mg/kg i.p.) at indicated times (FIG. 14A). Tumor volume was reduced (p=0.02) in mice co-administered pHLIP-PNA3+CDDP compared to pHLIP-control PNA+CDDP (FIG. 13A). Tumor volume in mice treated with either pHLIP-PNA alone was similar to vehicle-treated mice (FIG. 14A). Importantly, survival of mice treated with pHLIP-PNA3 vs. mock was increased 1.6-fold (39 vs. 25 days; FIG. 13B), and body weight was similar among groups (FIG. 14B), showing that PNAs are non-toxic in vivo.

Figure 13C:
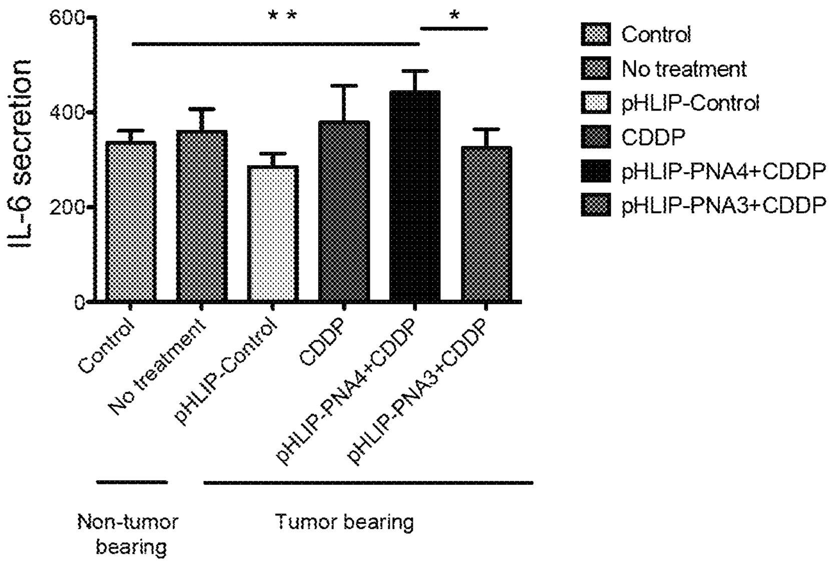
FIG. 13C is a bar graph showing blood IL-6 levels after the various noted treatments. Asterisks indicate P<0.05 (*) or P<0.01 (**).
Figure 13D:
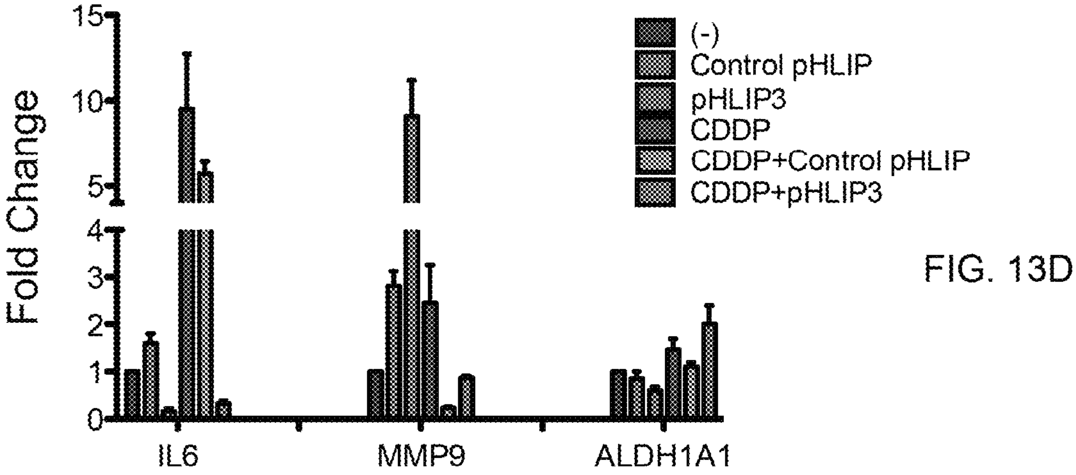
FIG. 13D is a bar graph showing tumor expression levels for IL-6, MMP9, and ALDH1A1 in mice treated with pHLIP-PNA3 compared to control.

Example 4. Combination pHLIP-PNA3-Cisplatin Treatment Decreases HOTAIR Targets In Vivo A positive correlation between tumor growth and the pro-inflammatory cytokine IL-6 has been described (see FIG. 5). HOTAIR has been demonstrated to upregulate both IL-6 and MMP-9 in ovarian cancer cells. In an exemplary method, it was of interest to examine the effect of PNA3 on IL-6 in vivo. In tumor-bearing mice, blood IL-6 levels were similar before tumor formation and after the first bi-weekly treatment of pHLIP-PNA and/or CDDP. However, after the second bi-weekly treatment, blood IL-6 levels increased ($p<0.01$) after treatment with CDDP alone or pHLIP-control PNA+CDDP compared to controls (FIG. 13C), indicating that CDDP induced tumor IL-6 secretion. Moreover, IL-6 blood levels were reduced ($P<0.05$) after pHLIP-PNA3+CDDP treatment compared to pHLIP-PNA control+CDDP (FIG. 13C), presumably due to pHLIP-PNA3-mediated HOTAIR inhibition and subsequent inhibition of CDDP-stimulated IL-6. In addition, IL-6, MMP-9 and ALDH1A1 tumor levels were examined. Reduced ($P<0.05$) expression of IL-6, MMP-9 and ALDH1A1 was observed in mice treated with pHLIP-PNA3 compared to control (FIG. 13D). Taken together, the results show that pHLIP-PNA3-mediated HOTAIR inhibition reduces IL-6, MMP-9, and ALDH1A1 expression, increases CDDP sensitivity, and subsequently improves overall survival.

Figure 13E:
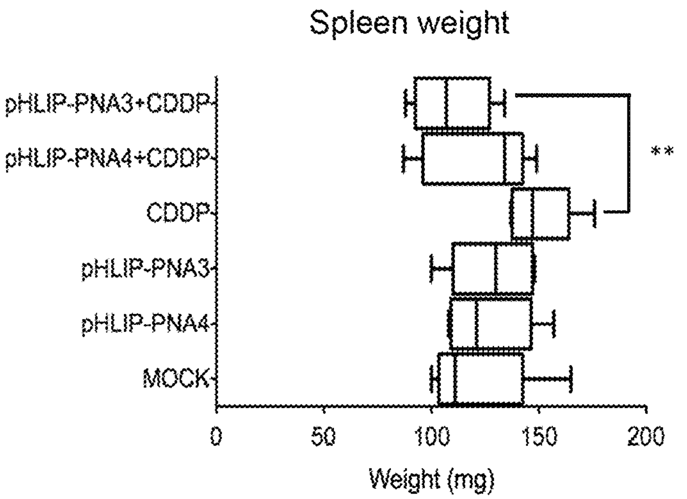
FIGS. 13E-13F are whisker plots showing the effect of the noted treatments on spleen (E) and liver (F) weight. Asterisks indicate P<0.05 (*) or P<0.01 (**).
Figure 13F:
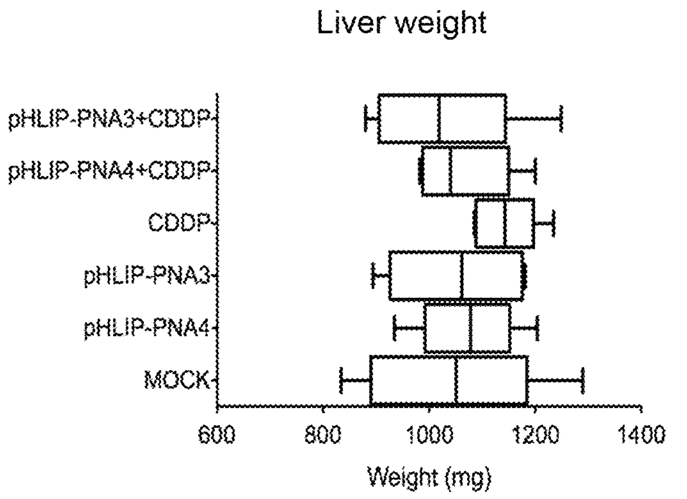
Figure 15:
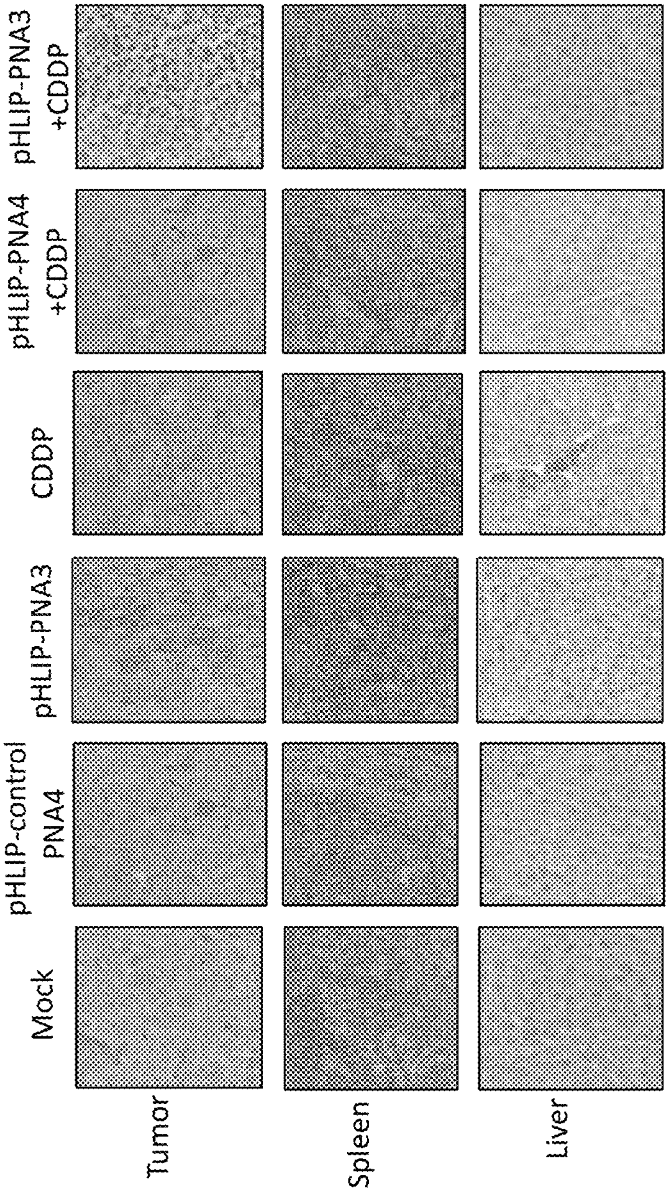
FIG. 15 is a series of images showing representative hematoxylin and eosin (H&E) slides of tumor, spleen, and liver from mice treated with the noted treatments.

In another exemplary method, in addition to tumor growth, it was of interest to examine spleen and liver weight and histology, as a strong association of platinum-based treatment and increased size of these organs has been reported. CDDP treatment increased ($P<0.01$) spleen size compared to mock treated (FIG. 13E), but interestingly the combination of pHLIP-PNA3 with CDDP abrogated ($p<0.01$) the CDDP-induced increase in spleen size (FIG. 13E). Although a similar trend for these effects on liver size was observed (FIG. 13F), none were statistically significant. No apparent histological changes (based on H&E staining) were seen (spleen, FIG. 13D; liver, FIG. 15B), but fewer cells in H&E slides of tumors from CDDP-treated mice (FIG. 15) indicated cell death.

The results described in the Examples demonstrate that pHLIP-PNA3 was effective despite an acidic tumor microenvironment, showing that this approach can overcome the impact of the Warburg effect, a well-known fundamental aspect of malignant transformation. The results also show that pHLIP-PNA3 can be safely (no change in body weight) and effectively (based on reduced tumor burden) combined with cytotoxic chemotherapy, including platinum-based drugs currently used in the clinic. pHLIP-PNA3 treatment lowered both tumor and blood levels of IL-6, showing that impacting the local (tumor) microenvironment can result in systemic (peripheral) effects. This is the first showing of a pHLIP targeting of an lncRNA in vivo.

The results described herein further show that targeting HOTAIR is a viable method for improving the efficacy of CDDP, and targeting HOTAIR with pHLIP-PNA can be co-administered with CDDP in HOTAIR-overexpressing cancers, such as breast, ovarian, prostate, pancreatic, and colon cancers. By targeting and inhibiting HOTAIR in vivo, tumors are resensitized to cisplatin, and survival increases.

Example 5. Treatment of Ovarian Cancer

In one exemplary embodiment, a subject having ovarian cancer can be treated using a HOTAIR-targeting synthetic polynucleotide analog described herein. The subject can be treated with a pharmaceutically effective amount of a pharmaceutical composition comprising a peptide nucleic acid comprising a nucleic acid sequence of SEQ ID NO: 14. The subject can be administered the pharmaceutical composition prior to administration of a traditional chemotherapeutic agent (e.g., cisplatin and/or etoposide), or concurrently with the administration of the traditional chemotherapeutic agent. The synthetic polynucleotide analog and traditional chemotherapeutic agent can be administered together in the same pharmaceutical composition, or can be administered separately in two distinct pharmaceutical compositions.

The pharmaceutical composition comprising the HOTAIR-targeting synthetic polynucleotide analog can be administered to the subject having ovarian cancer intratumoraly (i.e., directly into a solid ovarian tumor), intravenously, or orally. The pharmaceutical composition can be administered to the subject in a single dose, or in multiple doses. Where the pharmaceutical composition comprising the HOTAIR-targeting synthetic polynucleotide analog is administered to the subject concurrently with a traditional chemotherapeutic agent, the pharmaceutical composition comprising the HOTAIR-targeting synthetic polynucleotide analog can be administered to the subject according to current treatment protocols for ovarian cancer (e.g., every 21 days for three to six cycles). The pharmaceutical composition can be administered between treatments with a traditional chemotherapeutic. The pharmaceutical composition can be administered daily, every two days, every three days, every four days, every five days, every six days, weekly, bi-weekly, or monthly. In one exemplary embodiment, the pharmaceutical composition can be administered daily for a period of 1 to 7 days prior to a scheduled treatment with a traditional chemotherapeutic.

Example 6. Treatment of Breast Cancer

In one exemplary embodiment, a subject having breast cancer can be treated using a HOTAIR-targeting synthetic polynucleotide analog described herein. The subject can be treated with a pharmaceutically effective amount of a pharmaceutical composition comprising a peptide nucleic acid comprising a nucleic acid sequence of SEQ ID NO: 14. The subject can be administered the pharmaceutical composition prior to administration of a traditional chemotherapeutic agent (e.g., cisplatin and/or etoposide), or concurrently with the administration of the traditional chemotherapeutic agent. The synthetic polynucleotide analog and traditional chemotherapeutic agent can be administered together in the same pharmaceutical composition, or can be administered separately in two distinct pharmaceutical compositions.

The pharmaceutical composition comprising the HOTAIR-targeting synthetic polynucleotide analog can be administered to the subject having breast cancer intratumoraly (i.e., directly into a solid ovarian tumor), intravenously, or orally. The pharmaceutical composition can be administered to the subject in a single dose, or in multiple doses. Where the pharmaceutical composition comprising the HOTAIR-targeting synthetic polynucleotide analog is administered to the subject concurrently with a traditional chemotherapeutic agent, the pharmaceutical composition comprising the HOTAIR-targeting synthetic polynucleotide analog can be administered to the subject according to current treatment protocols for breast cancer. The pharmaceutical composition can be administered between treatments with a traditional chemotherapeutic. The pharmaceutical composition can be administered daily, every two days, every three days, every four days, every five days, every six days, weekly, bi-weekly, or monthly. In one exemplary embodiment, the pharmaceutical composition can be administered daily for a period of 1 to 7 days prior to a scheduled treatment with a traditional chemotherapeutic.

Example 7. Materials and Methods

Cell Lines, Culture Conditions and Reagents.

Epithelial ovarian cancer cell lines (A2780, A2780_CR5, KURAMOCHI) were maintained in RPMI 1640 medium. Breast cancer cell lines (MCF-7, MDA-MB-231 and SKBR3) were maintained in EMEM or McCoys media (Invitrogen, Carlsbad, Calif.). Cisplatin-resistant A2780_CR5 was established by continuous exposure to cisplatin. Cell lines were authenticated in 2012 by ATCC and tested for mycoplasma contamination (Manassas, Va.). Cisplatin (CDDP) was purchased from Calbiochem (Billerica, Mass.), and etoposide was purchased from Santa Cruz Biotech. (Santa Cruz, Calif.). LZRS-HOTAIR was Addgene plasmid #26110. Full-length HOTAIR was cloned into pAV5S vector containing a 98-mer aptamer sequence and as a vector control, aptamer cloned into pAV5S was used to account for any possible RNA-dependent signaling effects.

Proliferation MTT Assays.

The quantity of viable cells was calculated by 3-(4,5-dimethylthiazol-2-yl)-2,5-diphenyltetrazolium bromide (MTT) assay. Cells were grown in 6 cm culture plates until 70% confluence and treated with either PNA3 or control PNA (1 μM final) for 24 hrs. Next day, the plates were trypsinized, counted and $2\times10^3$ cells were seeded into 96-well plates in triplicate at indicated times. Absorbance (570 nm; filter reference at 620 nm) was recorded using EnVision Multilabel Plate Reader (Perkin Elmer, Waltham, Mass.).

Clonogenic Survival Assays.

Cells were grown in 6 cm culture plates until 70% confluence and treated with either PNA3 or control PNA (1 μM final) for 24 hr. Next day, the plates were trypsinized, serially-diluted and 500 cells were seeded into 6-well plates in triplicate. Next day, cells were treated with CDDP (0, 15, 30 45 μM) or etoposide (5 μM) for 3 hrs, washed, allowed 6-8 days of cell growth for colony formation, stained with 5% crystal violet, and counted. Percent survival of treated cells was calculated relative to untreated samples.

Cell Invasion Assays.

Cells were grown in 6 cm culture plates until 70% confluence and treated with either PNA3 or control PNA (1 μM final) for 24 hr. Next day, the plates were trypsinized, serially diluted and 50,000 cells were seeded inside a matrigel invasion chamber insert (Corning, Cat #354480) in serum-free media supplemented with 0.1% BSA. Media supplemented with 20% FBS was added to the bottom of the well and 48 hrs later, cells were fixed and dyed using Wright-Giemsa method (Hema 3 Stat pack, Cat #23-122-929) and invasion was counted under a light microscope at 20× magnification. Relative cell invasion was measured by dividing the control number of invaded cells by the PNA-treated samples.

In Vitro Transcription RNA.

Full length T7-promoter-driven HOTAIR and ALU cDNAs were cloned into pcDNA3.1 with a single NHEI restriction site after the transcription stop site. Vector (1 μg) was linearized by NHEI digestion followed by PCR cleanup (Qiagen, PCR clean-up kit). Eluted DNA was in vitro transcribed into RNA according to manufacture's protocol (New England Biolabs, Cat # E2040S,). The total RNA was purified according to manufacturer's protocol (Qiagen, RNA clean-up kit). Total RNA (1 μg) was treated with DNAseI according to manufacturer's protocol (Thermo Scientific, Cat # EN0525). DNAse treated RNA was purified using an RNeasy Mini kit (Qiagen).

Biotinylation and Folding of In Vitro Transcribed RNA.

Purified RNA (1.67 μM) was 3'-biotinylated according to manufacturer's protocol (Thermo Scientific, Cat #20160). After biotinylation, RNA was purified according to manufacturer's protocol (Qiagen, RNA clean-up kit). Total purified RNA was folded into native structure in folding buffer (100 mM KCl, 50 mM Tris-HCl, 5 mM MgCl2, 0.1 mM CaCl2, 0.5 mM ZnCl2,) by heating to 100° C. for 5 minutes and then snap-cooled by placing into ice for 10 min.

In Vitro Immunoprecipitation Assay.

100 ng of folded 3' biotinylated ALU or HOTAIR RNA was incubated with individual peptide nucleic acids (PNAs) (5 μM final) (n=6; PNA 1: 5'-TACTGCAGGC-3' (SEQ ID NO: 12), PNA 2: 5'-GTAACTCTGGG-3' (SEQ ID NO: 13), PNA 3: 5'-TCTGTAACTC-3' (SEQ ID NO: 14), PNA 4: 5'-CTCCCCTACTGC-3' (SEQ ID NO: 15), and PNA 5: 5'-CCCTCTCTCC-3' (SEQ ID NO: 16), and control PNA 6: 5'CTCCCTTCAA-3' (SEQ ID NO: 17)) PNA Bio (Thousand Oaks, Calif.) in 10 μL of 1× folding buffer supplemented with RNAse inhibitor (Thermo Scientific, Cat # AM2694) and bovine serum albumin (5 μg BSA) for 30 min at 37° C. Next, streptavidin HRP antibody (0.5 μL of 200 ng/uL, Cell Signaling) (Table 3) was added with 500 μL of binding buffer supplemented with RNAse inhibitor and 10% glycerol (IP Buffer) to each reaction and incubated at 4° C. for 1 hr. Next, 25 μL of protein A/G plus agarose beads were added (Santa Cruz Biotechnology) and placed into 4° C. rotator for 1 hr. The beads were washed 3 times with 1× IP Buffer supplemented with RNAsein. Recombinant polycomb repressive complex 2 (PRC2, 0.1 nM final, Active Motif, cat #31387) was added and incubated for 3 hr at 4° C. rotator. After incubation, beads were washed 3× with 1× IP buffer supplemented with RNAsein. Samples were then boiled in 1× sample buffer for 5 min at 100° C. and run on BioRad precast polyacrylamide gel.

Synthesis of PNAs and pHLIP-AntiLinc Constructs.

PNAs were purchased (PNA Bio) containing cell-penetrating peptide (CPP) RRRQRRKKR (SEQ ID NO: 19) and used in in vitro cell biology experiments. The pHLIP peptide was purchased from New England Peptide: AAEQNPIYWARYADWLFTTPLLLLDLALLVDADEGT(CNPys)G (SEQ ID NO: 18). In order to generate pHLIP-antilnc constructs, PNAs that did not contain CPPs were conjugated to the C-terminus of thiolated pHLIP using a cysteine group derivatized with 3-nitro-2-pyridinesulphenyl (NPys) similar to the recently published report (Cheng, C. J., et al., *MicroRNA silencing for cancer therapy targeted to the tumour microenvironment*. Nature, 2015. 518(7537):107-11.). To synthesize pHLIP-anti-lnc constructs, pHLIP-Cys (NPys) and anti-lnc PNA (peptide:PNA of 1:1.3) were reacted overnight in the dark in a mixture of DMSO/DMF/0.1 mM KH2PO4 pH 4.5 (v/v 3:1:1). The thiolated PNAs used in the study are listed in Table 1.

TABLE 3

| Antibodies |
|---|
| Gene |
| EZH2 |
| Streptavidin HRP |
| H3K27me3 |
| H3 |
| β-tubulin |
| Secondary Antibody |
| Goat anti-Rabbit |
| Goat anti-mouse |

Caspase 3/7 Cleavage Assay.

Cells were grown in 6 cm culture plates until 70% confluence and treated with either PNA3 or control PNA (1 μM final) for 24 hr. Next day, the plates were trypsinized, counted and $2\times10^4$ cells were seeded into 96-well plates in triplicate. 24 hrs later cells were either not treated or treated with CDDP (20 μM) or etoposide (10 μM) for 3 hrs, washed with 1×PBS and fresh media was added and incubated at 37° C. for 24 hrs. Cleaved Caspase 3/7 activity, indicative of apoptosis, was detected according to manufacturer's protocol (Promega, Cat # G8090).

Aldefluor Assay and Flow Cytometry.

ALDH1 enzymatic activity was measured using the Aldefluor assay kit (Stemcell Technologies, Vancouver, Canada) following the manufacturer's instructions. Briefly, $1\times10^6$ cells were resuspended in Aldefluor assay buffer containing the ALDH1 substrate, bodipyaminoacetaldehyde (BAAA) at 1.5 mM or 2.4 mM, and incubated for 30 minutes at 37° C. The test ALDH1A1-positive population was gated using control cells incubated under identical conditions with the ALDH inhibitor, diethylamino benzaldehyde (DEAB). The relative increase in Alexa-Fluor 488 signal of the ALDH-positive cells was determined by a FACS Aria II flow cytometer (BD Biosciences, San Jose, Calif., USA). For each experiment, 50,000 events were analyzed using Cell Quest software (B-D Biosciences, version 3.3, San Jose, Calif., USA) and the relative percentage of ALDH(+) cells was calculated compared to DEAB treated cells.

ChIPNA Assay.

MCF-7 cells were grown to 80% confluence and then 1 μM of biotinylated PNA3 or control PNA was added. 24 hrs later cells were trypsinized, pelleted, washed with 1×PBS and half of the pellet was fixed with 4% formalin solution. For each sample, the nuclei were isolated using cytoplasmic lysis buffer and then they were resuspended in nuclei ChIP lysis buffer, sonicated on HIGH for 30 sec on/30 sec off for 1 hr. The lysate was spun at 13 k RPM at 4° C. for 10 mins Anti-streptavidin antibody (Cell signaling cat #) was added to the soluble fraction for 2 hrs followed by binding of protein A/G plus agarose beads (SC catalog number) for an additional 2 hrs at 4° C. Beads were washed 3 times with wash buffer at 4° C. and then Proteinase K treated. Nucleic acid was separated with TRIzol. The RNA was purified using RNAeasy column (Qiagen) and eluted in nuclease-free water. The RNA eluate was treated with DNAseI per manufacturers protocol, heat inactivated for 15 min at 65° C. to completely inactivate any remaining DNAse. 1 μL of RNA isolate was used per well for qRT-PCR analysis to confirm lncRNA retrieval. LncRNA FIRRE was used as a negative control, LncRNA ANRIL was used as a positive control.

Mouse Xenograft Experiments.

All animal studies adhered to ethical regulations and protocols. To assess tumorigenicity of cells, cultured A2780_CR5 cells were washed with PBS trypsinized and counted with trypan blue, re-suspended in 1:1 PBS/matrigel (BD Bioscience) and $2\times10^6$ cells were injected subcutaneously into the left flank of 3- to 4-week-old female nude athymic mice (BALB/c-nu/nu; Harlan, Indianapolis, Ind.). Engrafted mice (n=6 per group) were inspected three times per week for tumor appearance by visual observation and palpation. Once tumors were ~200 $mm^3$, mice were treated with either CDDP (2 mg kg−1) or PNA (1 mg kg−1) or both CDDP and PNA twice per week for two weeks. Blood samples were collected by puncturing the left lateral saphenous vein with a needle and collected using a capillary tube. Tumor length (l) and width (w) were measured biweekly using digital calipers and tumor volume (v) was calculated as v=½×l×w2. No randomization was used and no animals were excluded from the final data. The investigator measuring tumor size was blinded to the treatment groups. Mice were sacrificed when tumor diameter reached 2 $cm^3$ or at the end of study.

ELISA and Cytokine Release Assays.

Conditioned media were prepared by washing culture plates with PBS followed by incubation in serum-free RPMI medium with antibiotics for 48 hr and stored at −80° C. Total cell counts were determined and ELISA was performed using kits and procedures from R&D systems (Minneapolis, Minn. Cytokine release assay, Cat # ARY005) and eBiosciences (San Diego, Calif. IL-6 ELISA Cat #88-7066-22). The data were normalized to the cell number and reported as fold change. IL-6 release assay was performed 3 times and the cytokine release assay was performed once. ELISA from blood samples were done by spinning the total blood at 13,000 RPM for 5 mins at 4° C. and 100 μL of the serum was added to each well of a 96-well plate.

Luciferase Assays, DNA Damage Experiments.

TOV112D cells were seeded in 96-well plates (104 cells/well) and transfected with pGL3-E-selectin vector (300 ng construct/transfection). To normalize transfection efficiency, cells were co-transfected with PGL4 *Renilla* plasmid (100 ng). Twenty-four hours after transfection, cells were treated with PNA3 or Control PNA (1 uM) for indicated times. Luciferase activity was analyzed using the Dual Luciferase Reporter Assay System (Promega, Madison, Wis.) and a Thermo Scientific Multilabel Plate Reader RNAi.

Forward primer 5'-GTGGTTTATCTTGCACCCCTCATTCTCAAGCCCCAGCCAGGGAA-3' (SEQ ID NO: 20), and reverse primer 5'-TTCCCTGGCTGGGGCTTGAGAATGAGGGGTGCAAGATAAACCAC-3' (SEQ ID NO: 21). The dsiRNA sequences used to target human HOTAIR (Sense strand 5'-UUCUAAAUCCGUUCCAUUCCACUGCGA-3' (SEQ ID NO: 22), and antisense strand 5'-/5Phos/GCAGUGGAAUGGAACGGAUUUAGAA-3' (SEQ ID NO: 23) or negative control RNA targeting GFP (Sense strand 5'-CUACAACAGCCACAACGUC-3' (SEQ ID NO: 24), and antisense strand 5'-/5Phos/GACGUUGUGGCUGUUGUAG-3' (SEQ ID NO: 25)). dsiRNAs were transfected into cells using Lipofectamine 2000 (Invitrogen). shRNA for p65 and control were purchased from Santa Cruz (Sc-29410-SH, and sc-108060). 48 hr post transfection, A2780p cells were selected with 2.5 ng/μL puromycin for 5 days and then maintained in 1 ng/μL of the drug.

Immunoblot Analysis.

Cells were lysed in RIPA lysis buffer (50 mM Tris-HCl, 150 mM NaCl, 1 mM EDTA, 1% NP-40, 0.5% sodium deoxycholate and 0.1% SDS) supplemented with protease inhibitors (Sigma). Protein (approximately 5-10 μg) was loaded on precast 7.5% TGX gels (BioRad, Hercules, Calif.), blotting was performed using polyvinylidene difluoride (PVDF) membrane (GE Healthcare, Pittsburg, Pa.). Membranes were blocked, incubated overnight at 4° C. with primary antibody (EZH2, H3K27me3, Histone 3, β-tubulin), washed, and then incubated with HRP-conjugated secondary antibody (Kirkegaard & Perry Laboratories, Gaithersburg, Md.) (Table 3), and protein signals were observed using a chemiluminescence system (Thermo Scientific, Schaumberg, Ill.), according to instructions provided by the manufacturer.

RNA Extraction and Quantitative RT-PCR (qPCR).

RNA was extracted from cell lines and tumors using RNeasy kit (Qiagen, Venlo, Limburg), cDNA was prepared using MMLV RT system (Promega), and qPCR was performed with total cDNA and primers for indicated genes and GAPDH or EEF1A as the endogenous control (Table 4), using Applied Biosystems 7500 Fast RT-PCR system (Life Technologies, Grand Island, N.Y.) and corresponding software.

moidal dose curve fitting. The estimate variation within each group was similar therefore student's t-test was used to statistically analyze the significant difference among different groups by using Prism 4.0 (GraphPad Software). The genome-wide analysis experiments were conducted as described previously (Miller, D. F., et al., *A new method for stranded whole transcriptome RNA-seq*. Methods, 2013. 63(2): 26-134 and Miller, D. F., et al., *Stranded Whole Transcriptome RNA-Seq for All RNA Types*. Current Protocols in Human Genetics, 2015: p. 11.14. 1-11.14. 23, both of which are incorporated herein in their entireties) using the Partek Genomics Suite (version 6.5). For mouse xenograft study, statistical significance was determined using student two-tailed t-test. Unless otherwise noted, no animals were excluded from the final data.

All of the compositions and methods disclosed and claimed herein can be made and executed without undue

TABLE 4

Primer sequences for NF-κB target genes and controls.

| qPCR oligos for HOTAIR target genes | Sense (5'-3') | SEQ ID | Antisense (5'-3') | SEQ ID |
|---|---|---|---|---|
| IL6R | TCACTGGGTGCTCAGGAAG | 26 | ACCAGCAAGTGCACAGTCC | 27 |
| MMP9 | TTGACAGCGACAAGAAGTGG | 28 | GCCATTCACGTCGTCCTTAT | 29 |
| NFKBIA | GCAAAATCCTGACCTGGTGT | 30 | GCTCGTCCTCTGTGAACTCC | 31 |
| IL6 | TACCCCCAGGAGAAGATTCC | 32 | TTTTCTGCCAGTGCCTCTTT | 33 |
| GAPDH | CCATCACTGCCACCCAGAAG | 34 | CCTTGCCCACAGCCTTGG | 35 |
| EEF1A | GCCCCAGGACACAGAGACTTTATC | 36 | CAACACCAGCAGCAACAATCAG | 37 |
| ABL2 | TTCCTGGTGCGAGAAAGTG | 38 | TACACTTGGGTGCTGGGTAG | 39 |
| LAMB3 | ACTATGCTGTGTCCCAGCTC | 40 | ACAGCGCTCACAATTTGG | 41 |
| LAMC2 | CTGCGAGAAGTGCAAGAATG | 42 | ATCCGTGAGCATGTGGAAG | 43 |
| PCDH10 | CTAAACACCAGCGAGCAGAG | 44 | TGTCTCCATGACCACTGTCC | 45 |
| PCDHB5 | GGTGGATGTGAATGACAACG | 46 | GAAAGGGGAGATCATTCTGG | 47 |
| JAM2 | AGGCCTATGGGTTTTCTGC | 48 | CTCCGACCCAGTTTCTTCC | 49 |
| HOXD12 | CTCAACTTGAACATGACAGTGC | 50 | AATCTGCTGCTTCGTGTAGG | 51 |
| HOXD13 | TGGAACAGCCAGGTGTACTG | 52 | AGCTGCAGTTTGGTGTAAGG | 53 |
| ALDH1A1 | TCCCGTTGGTTATGCTCATTTG | 54 | GGAGTTTGCTCTGCTGGTTTGAC | 55 |

Immunofluorescence Quantification.

TOV112 cells were plated on glass slides (50,000 cells/well) and incubated at 37° C., and 24 hrs later incubated with 100 nM cy3-pHLIP-PNA3 or cy3-pHLIP-Control PNA for 1 hr at 37° C., washed 3× with 1×PBS and then fixed with 10% formalin or vector control incubated overnight 4° C. with, and the number of cells displaying was determined in ten random images from 3 independent experiments using a light microscope (60× magnification).

Statistical Analysis.

All data are presented as mean values±SD of at least three biological experiments unless otherwise indicated. CDDP $IC_{50}$ values were determined by Prism 6 (GraphPad Software, San Diego, Calif.), using logarithm normalized sigexperimentation in light of the present disclosure. While the compositions and methods have been described in terms of particular embodiments, it is apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A synthetic polynucleotide analog molecule consisting of SEQ ID NO: 14, wherein the synthetic polynucleotide analog is a polynucleotide analog selected from the group consisting of a peptide nucleic acid, a peptide nucleic acid derivative, a locked nucleic acid, a morpholino, a bridged nucleic acid, a phosphorothioate oligonucleotide, and a 2'-O-methyl-substituted RNA.

2. The synthetic polynucleotide analog molecule of claim 1, wherein the synthetic polynucleotide analog is conjugated to at least one polypeptide selected from the group consisting of a cell penetrating peptide, a cell targeting peptide, and a ph Low Insertion Peptide (pHLIP).

3. The synthetic polynucleotide analog molecule of claim 2 wherein the synthetic polynucleotide is conjugated to a pHLIP comprising an amino acid sequence of SEQ ID NO: 18.

4. A pharmaceutical composition comprising the synthetic polynucleotide analog molecule of claim 1 and a pharmaceutically acceptable carrier.

5. The pharmaceutical composition of claim 4, further comprising at least one of a pharmaceutically acceptable excipient and a delivery vehicle.

6. The pharmaceutical composition of claim 4, further comprising at least one chemotherapeutic agent.

7. The pharmaceutical composition of claim 6, wherein the at least one chemotherapeutic agent comprises a platinum-containing chemotherapeutic selected from the group consisting of cisplatin carboplatin; oxaliplatin; nedaplating; triplatin tetranitrate; phenanthriplatin; picoplatin; and satraplatin, a topoisomerase inhibitor selected from the group consisting of etoposide; amsacrine; teniposide; and doxorubicin, or a combination thereof.

8. The pharmaceutical composition of claim 5, wherein the delivery vehicle comprises a liposome formulation.

9. A method of treating a condition characterized by overexpression of HOTAIR in a subject in need thereof, wherein the condition characterized by overexpression of HOTAIR is selected from the group consisting of ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma, pancreatic cancer, and rheumatoid arthritis, comprising administering to the subject a therapeutically effective amount of the pharmaceutical composition of claim 4.

10. The method of claim 9, wherein the condition characterized by overexpression of HOTAIR is ovarian cancer or breast cancer.

11. The method of claim 9, the method further comprising administering at least one chemotherapeutic agent to the subject.

12. The method of claim 11, wherein the at least one chemotherapeutic agent comprises a platinum-containing chemotherapeutic selected from the group consisting of cisplatin carboplatin; oxaliplatin; nedaplating; triplatin tetranitrate; phenanthriplatin; picoplatin; and satraplatin, a topoisomerase inhibitor selected from the group consisting of etoposide; amsacrine; teniposide; and doxorubicin, or a combination thereof.

13. The method of claim 11, wherein the at least one chemotherapeutic agent is administered to the subject at the same time as the therapeutically effective amount of the pharmaceutical composition of claim 4, or after administration of the therapeutically effective amount of the pharmaceutical composition of claim 4.

14. A method for resensitizing a cell to a chemotherapeutic agent comprising contacting a chemotherapeutic resistant cell with an effective amount of the synthetic polynucleotide analog molecule of claim 1, wherein the method is carried out in vivo or in vitro.

15. The method of claim 14, wherein the method is carried out in vivo in a subject having a condition characterized by overexpression of HOTAIR selected from the group consisting of ovarian cancer, breast cancer, colorectal cancer, bladder cancer, cervical cancer, lung cancer, non-small cell lung cancer, small-cell lung cancer, esophageal squamous cell carcinoma, nasopharyngeal carcinoma, renal cancer, epithelial ovarian cancer, endometrial carcinoma, gastric cancer, hepatocellular carcinoma, melanoma, glioma, and pancreatic cancer.

16. A composition comprising a synthetic polynucleotide analog molecule and a diluent, wherein the synthetic polynucleotide analog molecule consists of nucleic acid having a nucleotide sequence of SEQ ID NO: 14 conjugated to one or more fluorescent molecules or fluorophores.

17. The composition of claim 16, wherein the one or more fluorescent molecules comprise on or more molecules selected from the group consisting of fluorescein, green fluorescent protein, rhodamine, cyanine dyes, and Alexa dyes.

* * * * *